US006309370B1

(12) United States Patent
Haim et al.

(10) Patent No.: US 6,309,370 B1
(45) Date of Patent: *Oct. 30, 2001

(54) INTRACARDIAC DRUG DELIVERY

(75) Inventors: Shlomo Ben Haim, Haifa; Uri Yaron, Zichron Yaakov; Avraham Matcovitch, Nesher, all of (IL)

(73) Assignee: Biosense, Inc., New Brusnwick, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 10 days.

(21) Appl. No.: 09/019,453

(22) Filed: Feb. 5, 1998

(51) Int. Cl.[7] .............................. A61M 31/00; A61N 1/00
(52) U.S. Cl. .............................. 604/66; 607/120; 607/122
(58) Field of Search ........................... 604/131, 134–137, 604/156, 157, 523, 21, 65–67; 607/120, 122; 600/508, 513

(56) References Cited

U.S. PATENT DOCUMENTS

| 4,296,100 | 10/1981 | Franco | 424/108 |
|---|---|---|---|
| 4,332,893 | 6/1982 | Rosenberg | 435/68 |
| 4,353,888 | 10/1982 | Sefton | 424/25 |
| 4,378,347 | 3/1983 | Franco | 424/108 |
| 4,503,038 | 3/1985 | Banda et al. | 424/95 |
| 4,578,061 | 3/1986 | Lemelson | 604/164 |
| 4,588,395 | 5/1986 | Lemelson | 604/59 |
| 4,636,195 | 1/1987 | Wolinsky | 604/53 |

(List continued on next page.)

FOREIGN PATENT DOCUMENTS

| 0 618 225 A1 | 3/1994 | (EP) | C07K/5/06 |
|---|---|---|---|
| 0 710 657 A1 | 8/1996 | (EP) | C07D/263/24 |
| 0 908 194 A2 | 4/1999 | (EP) | A61M/25/01 |
| WO 94/11506 | 5/1994 | (WO) | C12N/15/12 |
| WO 95/01138 | 1/1995 | (WO) | A61F/2/06 |
| WO 95/25807 | 9/1995 | (WO) | C12N/15/86 |
| WO 95/29993 | 11/1995 | (WO) | C12N/5/10 |
| WO 96/05768 | 2/1996 | (WO) | A61B/5/06 |

(List continued on next page.)

OTHER PUBLICATIONS

Fishbein M., Maclean D., Maroko P. (1978) Experimental Myocardial Infarction in the Rat. American Journal of Pathology .90 (1): 57–70.

Grounds M., McGeachie J. (1987) A model of myogenesis in vivo, derived from detailed autoradiographic studies of regenerating skeletal musscle, challenges the concept of quantal mitosis. Cell and Tissue Research. 250:563–569.

Felgner P., Gadek T., Holm M., Roman R., Chan H., Wenz M., Northrop J., Ringold G., Danielsen M. (1987) Lipofection: A highly efficient, lipid–mediated DNA–transfection procedure. Proc. Natl. Acad. Sci. USA 84:7413–7417.

Swain J. (1989) Gene Therapy A New Approach to the Treatment of Cardiovascular Tissue. Circulation. 80:1495–1496.

Whalen G., Shing Y., Folkman J. (1989) The Fate of Intravenously Administered bFGF and the Effect of Herparin. Growth Factors. 1:157–164.

(List continued on next page.)

Primary Examiner—Sharon Kennedy
(74) Attorney, Agent, or Firm—Louis J. Capezzuto

(57) ABSTRACT

Apparatus for intracardiac drug administration, including a catheter which is inserted into a chamber of the heart and brought into engagement with a site in the heart wall. The catheter includes at least one position sensor, which generates signals responsive to the position of the catheter within the heart, and a drug delivery device, which administers a desired dose of a therapeutic drug at the site determined responsive to the signals from the position sensor.

85 Claims, 10 Drawing Sheets

U.S. PATENT DOCUMENTS

| | | | |
|---|---|---|---|
| 4,668,226 | 5/1987 | Omata et al. | 604/272 |
| 4,698,301 | 10/1987 | Weiss et al. | 435/41 |
| 4,699,788 | 10/1987 | Catsimpoolas et al. | 424/104 |
| 4,721,672 | 1/1988 | Vallee et al. | 435/70 |
| 4,769,362 | 9/1988 | Catsimpoolas et al. | 514/25 |
| 4,778,787 | 10/1988 | Catsimpoolas et al. | 514/25 |
| 4,824,436 | 4/1989 | Wolinsky | 604/53 |
| 4,871,356 | 10/1989 | Haindl et al. | 604/247 |
| 4,874,746 | 10/1989 | Antoniades et al. | 514/21 |
| 4,879,312 | 11/1989 | Kamarei et al. | 514/560 |
| 4,888,324 | 12/1989 | Catsimpoolas et al. | 514/25 |
| 4,891,225 | 1/1990 | Langer et al. | 424/428 |
| 4,895,838 | 1/1990 | Mccluer et al. | 514/54 |
| 4,900,673 | 2/1990 | Harper et al. | 435/199 |
| 4,916,073 | 4/1990 | Vallee et al. | 435/252.3 |
| 4,921,482 | 5/1990 | Hammerslag et al. | 604/95 |
| 4,940,730 | 7/1990 | Wakamatsu et al. | 514/560 |
| 4,966,847 | 10/1990 | Stacey et al. | 435/172.3 |
| 5,026,839 | 6/1991 | Moscatelli et al. | 536/27 |
| 5,073,492 | 12/1991 | Chen et al. | 435/240.2 |
| 5,112,946 | 5/1992 | Maione | 530/324 |
| 5,194,596 | 3/1993 | Tischer et al. | 530/399 |
| 5,195,968 | 3/1993 | Lundquist et al. | 604/95 |
| 5,219,739 | 6/1993 | Tischer et al. | 435/69.4 |
| 5,244,460 | 9/1993 | Unger et al. | 604/53 |
| 5,310,883 | 5/1994 | Seddon et al. | 530/399 |
| 5,318,957 | 6/1994 | Cid et al. | 514/8 |
| 5,328,470 | 7/1994 | Nabel et al. | 604/101 |
| 5,332,671 | 7/1994 | Ferrara et al. | 435/240.1 |
| 5,368,564 | 11/1994 | Savage | 604/95 |
| 5,368,592 | 11/1994 | Stern et al. | 606/33 |
| 5,383,923 | 1/1995 | Webster, Jr. | 607/125 |
| 5,385,148 | 1/1995 | Lesh et al. | 128/662.06 |
| 5,404,297 | 4/1995 | Birk et al. | 362/421 |
| 5,431,168 | 7/1995 | Webster, Jr. | 128/658 |
| 5,466,596 | 11/1995 | Breitman et al. | 435/240.2 |
| 5,470,831 | 11/1995 | Whitman et al. | 514/16 |
| 5,568,809 | 10/1996 | Ben-Haim | 128/656 |
| 5,580,859 | 12/1996 | Felgner et al. | 514/44 |
| 5,587,383 | 12/1996 | Takatani et al. | 514/300 |
| 5,588,432 | 12/1996 | Crowley | 128/660.03 |
| 5,602,301 | 2/1997 | Field | 800/2 |
| 5,607,918 | 3/1997 | Eriksson et al. | 514/12 |
| 5,641,743 | 6/1997 | Bohlen et al. | 514/2 |
| 5,641,756 | 6/1997 | Robinson | 514/44 |
| 5,652,225 | 7/1997 | Isner | 514/44 |
| 5,661,133 | 8/1997 | Leiden et al. | 514/44 |
| 5,674,192 | 10/1997 | Sahatjian et al. | 604/28 |
| 5,693,622 | 12/1997 | Wolff et al. | 514/44 |
| 5,698,531 | 12/1997 | Nabel et al. | 514/44 |
| 5,707,969 | 1/1998 | Nabel et al. | 514/44 |
| 5,733,727 | 3/1998 | Field | 435/6 |
| 5,780,052 | 7/1998 | Khaw et al. | 424/450 |
| 5,785,965 | 7/1998 | Pratt et al. | 424/93.21 |
| 5,792,453 | 8/1998 | Hammond et al. | 424/93.21 |
| 5,797,870 | 8/1998 | March et al. | 604/49 |
| 5,807,556 | 9/1998 | Mannion et al. | 424/198.1 |
| 5,830,879 | 11/1998 | Isner | 514/44 |
| 5,840,059 | 11/1998 | March et al. | 604/53 |
| 5,843,742 | 12/1998 | Natsoulis et al. | 435/172.3 |
| 5,845,646 | 12/1998 | Lemelson . | |
| 5,846,528 | 12/1998 | Podsakoff et al. | 424/93.23 |
| 5,858,351 | 1/1999 | Podsakoff et al. | 424/93.23 |
| 5,925,012 | 7/1999 | Murphy-Chutorian et al. | 604/30 |
| 5,964,757 | 10/1999 | Ponzi . | |
| 6,004,269 * | 12/1999 | Crowley et al. | 600/439 |
| 6,024,739 | 2/2000 | Ponzi et al. . | |
| 6,027,473 | 2/2000 | Ponzi . | |
| 6,055,453 | 4/2000 | Hofman . | |

FOREIGN PATENT DOCUMENTS

| | | | |
|---|---|---|---|
| WO 96/18303 | 6/1996 | (WO) | A01N/63/00 |
| WO 96/26742 | 9/1996 | (WO) | A61K/48/00 |
| WO 96/39830 | 12/1996 | (WO) | A01N/43/04 |
| WO 97/11720 | 4/1997 | (WO) | A61K/48/00 |
| WO 97/14307 | 4/1997 | (WO) | A01N/43/04 |
| WO 97/23256 | 7/1997 | (WO) | A61M/29/00 |
| WO 97/24981 | 7/1997 | (WO) | A61B/5/0215 |
| WO 97/29701 | 8/1997 | (WO) . | |
| WO 97/32990 | 9/1997 | (WO) | C12N/15/86 |
| WO 97/47253 | 12/1997 | (WO) | A61B/19/00 |
| WO 98/05307 | 2/1998 | (WO) | A61K/9/22 |
| WO 98/07878 | 2/1998 | (WO) | C12N/15/86 |
| WO 98/10085 | 3/1998 | (WO) | C12N/15/86 |
| WO 98/15575 | 4/1998 | (WO) | C07K/14/47 |
| WO 99/10014 | 3/1999 | (WO) | A61K/48/00 |
| WO 99/10485 | 3/1999 | (WO) | C12N/15/10 |
| WO 99/22655 | 5/1999 | (WO) | A61B/17/32 |
| WO 99/29251 | 6/1999 | (WO) | A61B/19/00 |
| WO 99/39624 | 8/1999 | (WO) | A61B/1/31 |

OTHER PUBLICATIONS

Nabel E., Plautz G., Boyce F., Stanley J., Nabel G. (1989) Recombinant Gene Expression in vivo Within Endothelial Cells of the Arterial Wall. Science. 244:1342–1343.

Pavlath G., Rich K., Webster S., Blau H. (1989) Localization of Nuscle gene products in muclear domains. Nature.337:570–573.

Friedmann T. (1989) Progress Toward Human Gene Therapy. Science.244:1275–1281.

Ralston E., Hall Z. (1989) Transfer of a Protein Encoded by a Single Nucleus to Nearby Nuclei in Multinucleated Myotubes. Science.244:1066–1069.

Thomasen D., Booth F. (1990) Stable incorporation of a bacterial gene into adult rat skeltal muscle in vivo. American Physiological Society. C578–C581.

Parker T., Parker S., Schneider M. (1990) Peptide Growth Factors Can Provoke "Fetal" Contractile Protein Gene Expression in Rat Cardiac Myocytes. J. Clin. Invest. 85:507–514.

Shubeita H., McDonough P., Harris A., Knowlton K., Glembotski C., Brown J., Chien K. (1990) Endothelin Induction of Inositol Phospholipid Hydrolysis, Sacromere Assembly, and Cardiac Gene Expression in Ventricular Myocytes. J. of Biological Chemistry. 265 (33):20555–20562.

Wolff J., Malone R., Williams Ph, Chong W., Acsadi G., Jani A., Felgner P. (1990) Direct Gene Transfer into Mouse Muscle in Vivo. Science.247:1465–1468.

Nabel e., Plautz G., Nabel G. (1990) Site–Specific Gene Expression in Vivo by Direct Gene Transfer into the Arterial Wall. Science. 249:1285–1288.

Barr E., Leiden J. (1991) Systemic Delivery of Recombinant Proteins by Genetically Modified Myoblasts. Science. 254: 1507–1509.

Dhawan J., Pan L., Pavlath G., Travis M., Lanctot A., Blau H. (1991) Systemic Delivery of Human Growth Hormone by Injection of Genetically Engineered Myoblasts. Science. 254: 1509–1512.

Unger E., Banai S., Shou M., Jaklitsch M., Hodge E., Correa R., Jaye M., Epstein S. (1993) A model to assess interventions to improve collateral blood flow: continuous administration of agents into the left coronary artery in dogs. Cardiovascular Research. 27:785–791.

Edelman E., Nugent M., Karnovsky M. (1993) Perivascular and intravenous administration of basic fibroblast growth factor: Vascular and solid organ deposition. Proc. Natl. Acad. Sci. USA. 90:1513–1517.

Abstract: Blau R. (1994) Primary mouse myoblast purifaction, characterization, and transplantation for cell–mediated gene therapy. J. Cell biol. 125 (6):1275–87.

Kazumasa H., Grossman W., Friedman M., Edelman E., Prasad P., Keighley C., Manning W., Sellke Chronically Ischemic Porcine Hearts. Clinical Invest. 94:623–630.

Van Meter C., Claycomb W., Delcarpio J., Smith D., DeGruiter H1, Smart F., Ochsner J. (1995) Myoblast Transplantation in the Porcine Model: A Potential Technique for Myocardial Repair. The Journal of Thoracic and Cardiovascular Surgery. 110(5): 1442–1448.

Abstract: Chiu R., Zibaitis A., Kao R. (1995) Cellular cardiomyoplasty: myocardial regeneration with satellite cell implantation. Ann. Thorac. Surg. 60(1):12–18.

Abstract: Yoon P., Kao R., Magovern G. (1995) Myocardial regeneration. Transplanting satellite cells into damaged myocardium. Tex. Heart Inst. J. 22(2):119–125/.

Abstract: Taylor D., Atkins B., Hungspreungs P., Jones T., Reedy M., Hutcheson K.,Glower D., Kraus W. (1998) Regenerating functional myocardium: improved performance after skeletal myoblast transplantation. Nat. med. 4(8):929–933.

Li R., Mickle D., Weisel R., Mohabeer M., Zhang J., Rao V., Li G., Merante F., Jia Z. (1997) Natural History of Fetal Rat Cardiomyocytes Transplanted into Adult Rat Myocardial Scar Tissue. Circulation. 96(9): 179–187.

Scorsin M, Hagege A., Marotte F., Mirochnik N., Copin H., Barnoux M., Sabri A., Samuel J., Rappaport L., Menasche P. (1997) Does Transplantation of Cardiomyocytes Improve Function of Infarcted Myocardium? Circulation. 96(9): 188–193.

Scorsin M., Marotte F., Sabri A., Le Dref O., Demirag M., Samuel J., Rappaport L., Menasche P. (1996) Can Grafted Cardiomyocytes Colonize Peri–Infarct Myocardial Areas? Circulation. 94(9):337–339.

Leor J., Patterson M., Quinones M., Kedes L., Kloner R. (1996) Tranplatation of Fetal Myocardial Tissue into the Infarcted Myocardium of Rat—A Potential Method for Repair of Infarcted Myocardium? Circulation. 94(9):332–336.

Li R., Jia Z., Weisel R., Mickel D., Zhang J., Mohabeer M., Rao V., Ivanov J. (1996) Cardiomyocyte Transplantation Improves Heart Function. Ann. Thorac. Surg. 62:654–661.

Abstract: Murray C., Wiseman R., Schwartz S., Hauschka S. (1996) Skelatal Myoblast transplatation for repair of myocardial necrosis. J. Clin. Invest. 11:2512–2523.

Abstract: Lopez J., Simons M. (1996) Local extravascular growth factor delivery in myocardial ischemia. Drug Delivery. 3(3):143–147.

Lopez J., Edelman E., Stamler A., Morgan J., Sellke F., Simons M. (1996) Local Perivascular Administration of Basic Fibroblast Growth Factor: Drug Delivery and Toxicological Evaluation. Drug Metabolism and Disposition. 24(8):922–924.

Simons M., Ware J. (1996) Food for Starving Hearts. Nature Medicine. 2(5):519–520.

Harada K., Friedman M., Lopez J., Wang S. Li J., Pottumarthi P., Pearlman J., Edelman E., Sellke F., Simons M. (1996) Vascular endothelial growth factor administration in chronic myocardial ischemia. The American Physiological Society.1791–1802.

Isner J. (1997) Angiogenesis for revascularization of ischaemic tissues. European Heart Journal. 18:1–2.

Abstract: Irintchev A., Langer M., Zweyer M., Theisen R., Wernig A. (1997) Functional improvement of damaged adult mouse muscle by implantation of primary myoblasts. J. Physiol. 500 (Pt 3): 775–785.

Abstract: Robinson S., Cho P., Levitsky H., Olson J., Hruban R., Acker M., Kessler P. (1996) Arterial delivery of genetically labeled skeletal myoblasts to the murine heart: long––term survival and phenotypic modification of implanted myoblasts. Cell Transplant. 5(1):77–91.

Abstract: Taylor D., Silvestry S., Bishop S., Annex B., Lilly R., Glower D., Krause W. (1997) Delivery of primary autologous skeletal myoblasts into rabbit heart by coronary infusion: a potential approach to myocardial repair. Proc. Assoc. Am. Physicians. 109(3):245–253.

Licking E. (1999) Gene Therapy—One Family's Story. Business Week. Jul.: 94–104.

Ware J., Simons M. (1997) Angiogenesis in ischemic heart tissue. Nature Medicine. 3(2): 158–164.

Taylor D., Atkins B., Hungspreugs P., Jones T., Reedy M., Hutcheson K., Glower D., Kraus W. (1998) Regenerating functional myocardium: Improved performance after skeletal myoblast transplantation. Nature Medicine. 4(8): 929–933.

Abstract: Dorfman J., Duong M., Zibaitis A., Pelletier M., Shum–Tim D., Li C., Chiu R. (1998) Myocardial tissue engineering with autologous myoblast implantation. J. Thorac. Cardiovasc. Surg. 116(5):744–751.

Schwartz Y. (1998) Therapeutic Angiogenesis Overview.

Val P., Losordo D., Tkebuchava T., chen D., Milliken C., Isner J. (1999) Catheter–Based Myocardial Gene Transfer Utilizing Nonfluoroscopic Electromechanical Left Ventricular Mapping. Journal of the American College of CArdiology. 34(1):246–254.

* cited by examiner

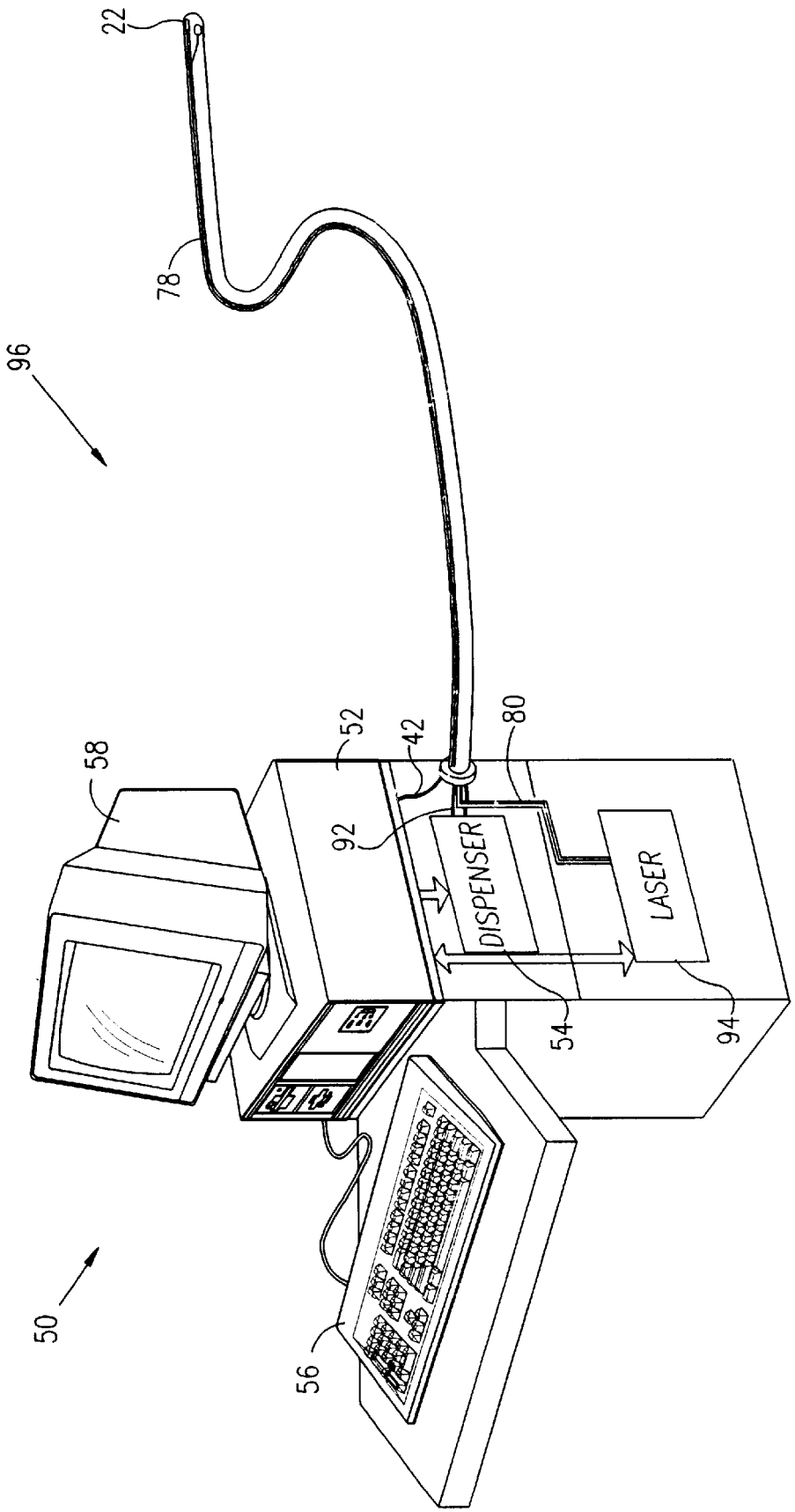

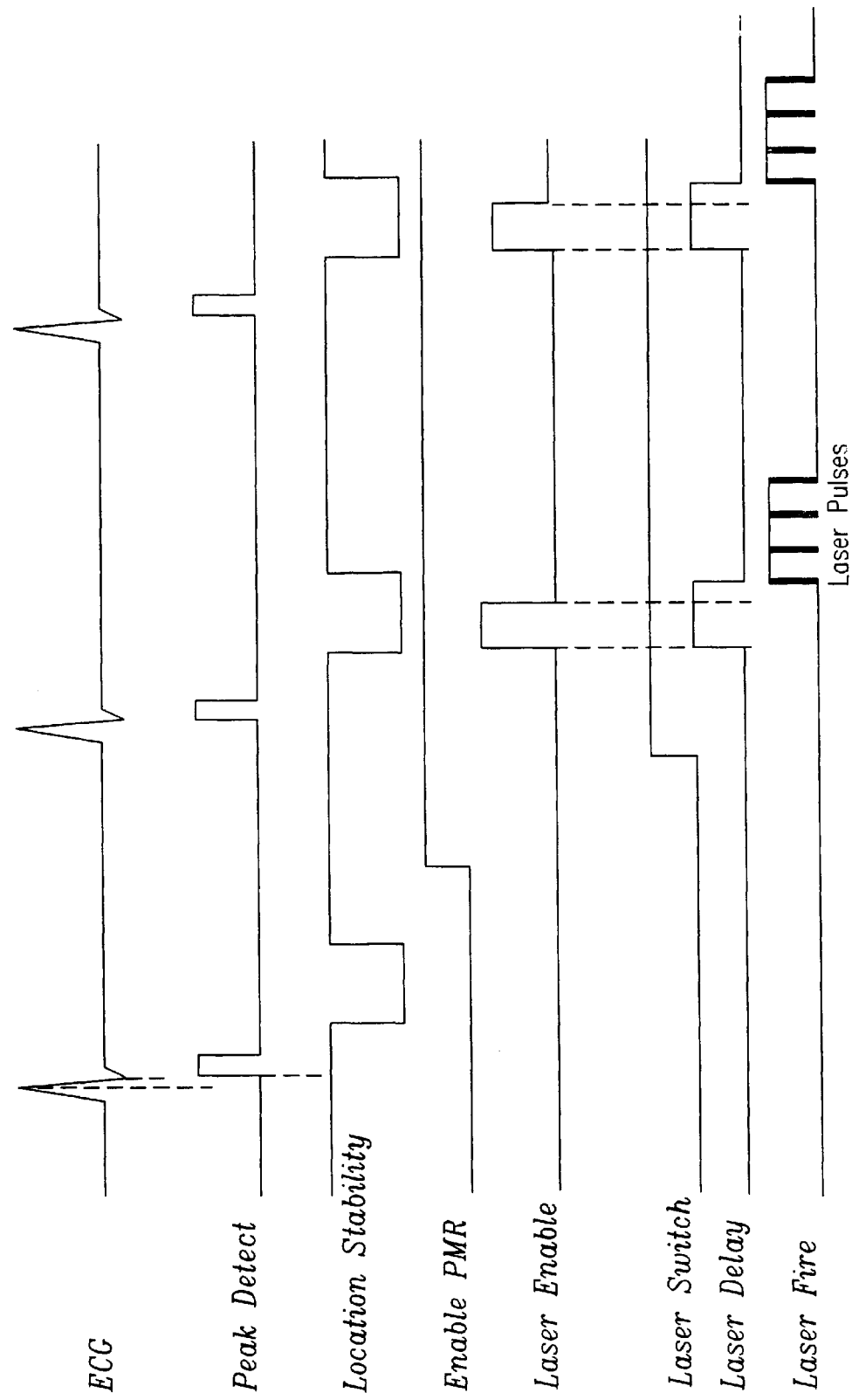

INTRACARDIAC DRUG DELIVERY

FIELD OF THE INVENTION

The present invention relates generally to methods and devices for invasive cardiac treatment, and specifically to methods and devices for minimally invasive treatment of cardiac ischemia.

BACKGROUND OF THE INVENTION

Heart disease or heart failure is still the major cause of death in the Western world. One of the most common forms of heart disease is the formation of ischemic regions within the myocardium resulting from poor blood perfusion, either due to chronic coronary arterial disease or following acute myocardial infarction. Cells within ischemic zones undergo a gradual, generally irreversible, degeneration process eventually rendering them dead (see M. C. Fishbein, M. B. McLean et al., Experimental myocardial infarction in the rat, Am. J. Pathol. 90: 57–70, 1978). This process is expressed as a corresponding progressive deterioration of the viability of the ischemic zone.

Currently available approaches for treating coronary arterial disease symptoms include methods of restoring blood flow to a large localized segment of the epicardial coronary arterial tree (angioplasty) and bypassing the obstruction within the coronary arteries entirely, by performing a bypass graft.

Drug administration, for example, administration of cytoprotective compounds which prolong anaerobic cell viability, and laser myocardial revascularization, which improves blood supply to an affected myocardial region, are further therapeutic approaches (some still under testing) for treating ischemia.

It has been observed in some cases of myocardial ischemia that new, collateral blood vessels may grow in the heart to augment the supply of oxygen to the ischemic tissue. This phenomenon is known as angiogenesis. Recent advances in the understanding of mechanisms governing such angiogenesis, based on naturally-occurring substances known as growth factors, such as vascular endothelial growth factors (VEGF) and fibroblast growth factors (FGF), have added a novel possible form of therapy based on administration of exogenous angiogenic growth factors to the heart.

Several mechanisms have been proposed to explain the observed beneficial effect of growth factors on alleviating chronic and/or acute ischemia. These mechanisms include angiogenesis, increase in myocyte viability and resistance to injury, restoration of ischemia-impaired endothelium-dependent vasomotion, and recruitment of preexisting collateral vessels (see, J. A. Ware and M. Simons, Angiogenesis in ischemic heart disease, Nature Medicine, 3(2):158–164, 1997, which is incorporated herein by reference).

Harada et al. (Basic fibroblast growth factor improves myocardial function in chronically ischemic porcine hearts, J. Clin. Invest., 94:623–630, 1994, which is incorporated herein by reference) report that periadventitial administration of basic fibroblast growth factor (bFGF) to pigs with gradual (artificially induced) coronary occlusion resulted in improvement of coronary flow and reduction in infarct size, as well as in prevention of pacing-induced hemodynamic deterioration. The growth factor was administered extraluminally to both occluded and neighboring arteries by applying a number of capsules holding beads containing bFGF and securing them to the artery. The beads were designed to slow-release their bFGF content at a predictable rate over a prolonged period of time, in order that the bFGF be effectively absorbed and transported to affected myocardial zones.

By comparison, intravenous administration of bFGF, including continuous systemic infusion, as opposed to periadventitial administration, was reported to exhibit only a minor angiogenic effect, mainly due to washout of the drug by the blood stream resulting in dilution, and a low retention time. (See E. R. Edelman et al., Perivascular and intravenous administration of basic fibroblast growth factor: Vascular and solid organ deposition, Proc. Natl Acad. Sci. USA, 90:1513–1517, 1993; G. F. Whalen et al., The fate of intravenously administered bFGF and the effect of heparin, Growth Factors, 1:157–164, 1989; and E. F. Unger et al., A model to assess interventions to improve collateral blood flow: continuous administration of agents into the left coronary artery in dogs, Cardiovasc. Res., 27:785–791, 1993, which are incorporated therein by reference).

In a later paper (K. Harada et al., Vascular endothelial growth factor administration in chronic myocardial ischemia, Am. J. Physiol. 270 [Heart Circ. Physiol. 39]: H1791–H1802, 1996, which is incorporated herein by reference), the authors report similar beneficial angiogenic effects of vascular endothelial growth factor (VEGF) in pigs. The VEGF was administered by a microcatheter placed adjacent to an ameroid constrictor (i.e., an external ring of appropriate internal diameter, which is placed around the artery in order to induce a gradual occlusion thereof) and secured directly to the heart musculature distal to the constrictor. The microcatheter was connected to an osmotic pump (ALZET®, from Alza, Palo Alto, Calif.) placed inside the chest wall, outside the pericardial cavity.

An alternative approach for stimulating angiogenesis is gene therapy. Simons and Ware (Food for starving heart, Nature Medicine, 2(5):519–520, 1996, incorporated herein by reference) report still another growth factor, FGF-5, as having the capability of inducing myocardial angiogenesis in vivo when administered using a gene transfer delivery approach employing adenoviral vectors as transfer agents. Similarly, J. M. Isner (Angiogenesis for revascularization of ischaemic tissues, European Heart Journal, 18:1–2, 1997, incorporated herein by reference) reports treatment of critical limb ischemia by intra-arterial administration of "naked DNA" including the gene encoding vascular endothelial growth factor (phVEGF). The solution of plasmid DNA is applied to the hydrogel coating of an angioplasty balloon, which retains the DNA until the balloon is inflated at the site of gene transfer, whereupon the DNA is transferred to the arterial wall.

Accumulated results seem to indicate that the drug delivery approach of choice for growth factors ought to be a local, rather than a systemic (intravenous), delivery approach. The preferability of local delivery may stem from the low half-life of injected bFGF and its short retention time. Prolonged systemic intravenous delivery of bFGF has been reported to result in the development of significant hematological toxicity, which did not completely resolve even 4 weeks after treatment, as well as hypotensive effects. In addition, dilution effects associated with washout of the drug by the blood stream render the drug quantities required for such an approach prohibitively high. (See J. J. Lopez et al., Local perivascular administration of basic fibroblast growth factor: drug delivery and toxicological evaluation, Drug Metabolism and Disposition, 24(8):922–924, 1996; and J. J. Lopez and M. Simons, Local extravascular growth factor delivery in myocardial ischemia, Drug Delivery, 3:143–147, 1996, which are incorporated herein by reference.)

Local sustained delivery, on the other hand, is free of at least some of the above-mentioned drawbacks and is apparently more effective. The main drawback of the local delivery approach employing present available techniques, as cited above, is its extensively invasive nature. The methods described in the articles cited above involve open chest surgery. Despite apparent physiological and therapeutic advantages, there is no currently available technique for effective, locally-targeted, minimally invasive technique for intracardiac drug delivery, particularly a technique based on controlled-release administration.

U.S. Pat. Nos. 4,578,061, 4,588,395, 4,668,226, 4,871,356, 5,385,148 and 5,588,432, which are all incorporated herein by reference, describe catheters for fluid and solid-capsule drug delivery to internal organs of a patient, generally for use in conjunction with an endoscope. The catheters typically comprise a needle or a tube disposed at a distal end thereof, communicating with a fluid or solid dispenser via a duct. None of the disclosed catheters, however, comprise means for accurate position-controlled delivery of therapeutic drugs.

SUMMARY OF THE INVENTION

It is an object of some aspects of the present invention to provide accurate minimally-invasive methods and apparatus for intracardiac administration of drugs to the myocardium.

In some aspects of the present invention, such methods and apparatus are used for accurate placement of controlled-release drug delivery devices.

In the context of the present patent application and in the claims, the term "controlled-release" is taken to refer to any and all techniques of sustained, controlled delivery of liquid or soluble compounds, including all forms of polymer-based slow-release and local continuous infusion.

Some aspects of the present invention are based on the finding described above that angiogenic growth factors, when properly administered to cardiac ischemic zones exhibiting marginal viability, induce and/or promote angiogenesis therein, thus augmenting blood perfusion. Preferably, the growth factors are administered at a known, predetermined depth within the heart tissue.

Accordingly, in preferred embodiments of the present invention, minimally-invasive intracardiac drug delivery (MI2D2) apparatus comprises a catheter having a distal end for insertion into a chamber of the heart. The catheter is used to administer a drug at one or more predetermined locations within the myocardium. The catheter comprises a position sensor, which is used to navigate and position the catheter adjacent to each of the one or more locations, and a drug delivery device, coupled to the dispenser, for administering a drug at the locations. The drug delivery device is disposed at or adjacent to the distal end of the catheter and injects or otherwise delivers the drug into the myocardium to an appropriate depth.

In some preferred embodiments of the present invention, the catheter also includes one or more physiological sensors, for diagnosis and identification of sites in the myocardium that are in need of drug administration. Preferably, the sensors are used to identify ischemic areas in which growth factors are to be administered. Most preferably, the physiological sensors are used in conjunction with the position sensor to produce a viability map of the heart, in accordance with which the drug is administered, as described further hereinbelow.

In some preferred embodiments of the present invention, the catheter is operated in conjunction with a drug dispenser, which meters and dispenses predetermined quantities of the drug, and a control circuit, for controlling and triggering the operation of the apparatus. The drug delivery device in the catheter preferably communicates with the dispenser via a suitable duct, i.e., a lumen or a tube extending along the length of the catheter. In preferred embodiments of the present invention, the catheter and associated drug delivery apparatus are used to administer growth factors to the myocardium, but it will be appreciated that the apparatus may similarly be used to accurately administer therapeutic agents of other types, as well.

Preferably, the position sensor comprises a magnetic position sensor, as described in PCT Patent publication number WO96/05768, which is incorporated herein by reference. Further preferably, the catheter includes a steering mechanism, for example, as described in U.S. Provisional Patent Application No. 60/042,872, which is assigned to the assignee of the present patent application and incorporated herein by reference. Alternatively, the steering mechanism may be of any suitable type known in the art, such as are described in PCT Patent Application PCT/US95/01103 or in any of U.S. Pat. Nos. 5,404,297, 5,368,592, 5,431,168, 5,383,923, 5,368,564, 4,921,482 and 5,195,968, all of which are incorporated herein by reference.

As mentioned above, accurate location of the drug administration site—relative to the borders of the ischemic region and the depth within the heart wall—is important in the successful completion of the treatment, and presence of excessive amounts of the growth factor in healthy tissue may have adverse effects thereon. Administration of the growth factor over an area that exceeds the borders of the ischemic region, or near the surface of the endocardial wall, where it may be washed away by the blood, compromises the therapeutic effectiveness of the treatment, poses toxic risks and adversely increases the drug amounts needed for achieving the desired therapeutic effects. Therefore, it is important to accurately navigate, locate and orient the catheter with respect to the ischemic regions designated for drug administration and to assure proper contact between the engaging surface of the catheter and the heart wall.

Accurate location and orientation of the catheter is accomplished using the position sensor and steering mechanism mentioned above. Furthermore, in some preferred embodiments of the present invention, the catheter comprises one or more proximity or contact sensors, for sensing and assuring contact between the catheter and the heart wall. In some of these preferred embodiments, the catheter comprises at least three contact sensors disposed on the surface of the catheter's distal end so as to assure proper contact between the catheter and the heart wall and ultimately, penetration of the injected drug to a desired depth.

In some preferred embodiments of the present invention, the catheter is navigated and located with respect to a viability map, which identifies areas of the heart muscle that are ischemic but still viable, as against adequately perfused areas on the one hand and infarcted, non-viable areas on the other. Such a map may be produced, for example, using methods described in U.S. Pat. No. 5,568,809 or in PCT Patent Application PCT/IL97/00010, which are incorporated herein by reference, wherein a geometrical map of the heart is generated indicating local viability levels. Preferably, ischemic areas to be treated are marked on the map with a grid of points at which the drug is to be injected by the catheter. Preferably, the map and grid are determined based on physiological activity of the heart indicative of local tissue viability, gathered in conjunction with location coordinates.

In some preferred embodiments of the present invention, viability mapping is carried out in conjunction with administration of the drug, using the same catheter. In these embodiments, the catheter comprises a sensor for determining viability or non-viability of the myocardial tissue. Such sensors may comprise one or more electro- or mechano-physiological detectors, which sense local myocardial electrical or mechanical activity, respectively, as described in the above-mentioned 5,568,809 patent and PCT/IL97/00010 PCT application. Alternatively or additionally, the sensor may comprise an optical sensor, preferably coupled to a suitable light source and fiberoptic light guides within the catheter, which detects autofluorescence of NADH in the myocardial tissue as an indication of the viability, as is known in the art.

Alternatively, the viability map may be generated in advance of drug administration, using one of the methods mentioned above, and fed to the control circuitry of the MI2D2 apparatus.

In some preferred embodiments of the present invention, the drug delivery device includes a hollow needle, preferably retractable, as described, for example, in U.S. Pat. Nos. 4,578,061, 4,668,226 and 5,588,432, mentioned above. The needle is retracted during insertion of the catheter into the heart and removal therefrom, but extends out of the distal end of the catheter to deliver the drug inside the heart. Preferably, the needle extends out through an opening which is sealed, using any suitable seal, such as a silicon septum, as is known in the art, so as to prevent a back-flow of blood into the catheter, while enabling the needle to be projected and retracted a multiple number of times. optionally, the needle itself may be sealed to prevent blood components from entering thereinto, using a valve, for example, as described in U.S. Pat. No. 4,871,356, mentioned above.

Preferably, the drug delivery device comprises a retraction mechanism coupled to the needle, which projects and retracts the needle into and out of the catheter, prior to and after drug delivery, respectively, and is capable of multiple projection/retraction cycles. Accordingly, the retraction mechanism may comprise a piston with a constrained stroke length, or another suitable device, as is known in the art. Preferably, a sensor is coupled to the retraction mechanism or to the needle itself, so as to sense when the needle has been fully projected out of the catheter and into the heart wall, prior to drug administration. Most preferably, the sensor also senses when the needle has been fully retracted into the catheter, to ensure that the catheter can be moved safely from one location to another. Preferably, drug administration is automatically disabled except when the catheter is in appropriate contact with a heart wall and the needle is projected to a desired length. Alternatively or additionally, a user of the apparatus is notified of the needle's position, with or without automatic disablement.

Further preferably, the drug delivery device or the dispenser comprises an occlusion detector, for example, a pressure sensor, ultrasonic transducer or flow-meter, as are known in the art, which senses the occurrence of any occlusion of the needle or flow obstruction along the duct. Such occlusion detection prevents pressure buildup, which may cause ruptures along the flow path of the drug, and assures reliable administration of the drug at the designated locations.

Typically, ischemic regions in the myocardium extend across areas of up to 10 cm$^2$, whereas the typical area of influence of a local growth factor injection is only a few mm$^2$. Employing a single needle for the administration of the growth factor to the whole affected region renders the procedure tedious and time-consuming. Accordingly, in alternative preferred embodiments of the present invention, the drug delivery device comprises a plurality of needles appropriately spaced from one another, connected to a drug feed manifold fed by the duct and capable of collective or independent projection-retraction motion.

In some preferred embodiments of the present invention, the administration of the drug by the catheter is gated in response to the heart rhythm. Preferably, the drug delivery device is controlled responsive to the thickness of the heart wall, which varies cyclically responsive to the heart rhythm. Thus, if the drug is delivered at end-diastole, for example, when the heart wall is generally thinnest, the drug will generally be dispersed most deeply into the myocardium.

In one such preferred embodiment, the catheter comprises an ultrasound sensor adjacent its distal end, which is used to measure the local thickness of the heart wall, as described, for example, in the above-mentioned PCT application PCT/US95/01103. The thickness measurement is used to gate the release of the drug, so that the drug is administered at an optimal depth within the myocardium, preferably 2–3 mm, as described above. Preferably, the heart wall thickness at a drug administration site is measured at several points in the cardiac cycle, and the thickness measurements are used in determining at what point in the cycle to administer the drug and in controlling the drug delivery device to release the drug accordingly.

Although preferred embodiments of the present invention are described herein mainly with reference to drug administration, it will be appreciated that these methods of gating to heart wall thickness may also be applied to other types of cardiac therapies. For example, thickness-gating may be used advantageously in ablating cardiac tissue for treatment of arrhythmias or in laser myocardial revascularization (LMR). Methods and apparatus for LMR are described, for example, in PCT Patent Application PCT/IL97/00011, whose disclosure is incorporated herein by reference. In some of these methods, known commonly as percutaneous myocardial revascularization (PMR), a catheter is inserted into the heart, and a laser beam is conveyed by a waveguide in the catheter to create channels through the endocardium into the myocardium. In others of these methods, known as transmyocardial revascularization (TMR), a probe is inserted through the chest wall and used to create channels that penetrate into a chamber of the heart through the epicardium and the myocardium.

Thus, in some preferred embodiments of the present invention, a laser used in LMR is gated responsive to the heart wall thickness. Preferably, when LMR is performed using the PMR method, the laser is gated to fire during systole, when the heart wall is generally thickest, so as to minimize the risk that the laser channel will penetrate all the way through the heart wall and out through the epicardium. On the other hand, when the TMR method is used, the laser may be gated to fire during diastole, so as to penetrate through the heart wall with a minimum of expended laser energy.

In some preferred embodiments of the present invention, LMR is used in conjunction with growth factor administration to enhance angiogenic effects. In these embodiments, an integrated catheter comprises a waveguide coupled to a LMR laser source and to suitable optics at the catheter's distal end, along with the elements for intracardiac drug delivery described above. The laser is operated to produce LMR channels in the myocardium, and a dose of the growth factor is then inserted into some or all of the channels. The use of the growth factor in conjunction with LMR is believed to further facilitate angiogenesis within cardiac ischemic regions (see, for example, J. A. Ware and M. Simons, cited above).

In these preferred embodiments, the growth factor drug is preferably contained in a slow-release capsule, made of an appropriate solid drug delivery medium, as described, for example, in U.S. Pat. No. 4,588,395 or 4,578,061, mentioned above. The capsule is inserted into the LMR channel or may, alternatively, be forced into the myocardium without the use of LMR. Preferably, the capsule is designed so that its dimensions remain substantially constant throughout the treatment period, so as to secure the capsule in place at the designated location and preclude accidental drift, thus assuring appropriate localized administration of the drug throughout the treatment duration.

In other preferred embodiments of the present invention, the growth factor or other drug is administered in conjunction with irradiation of the heart tissue with other types of radiation, for example, RF or ultrasound irradiation.

In some preferred embodiments of the present invention, in which the growth factors or other drugs are injected into the myocardium in a liquid form or as slow-release microcapsules dispersed in a liquid carrier, the drug dispenser comprises a metering pump, coupled to the catheter's proximal end. Such pumps are known in the art, including, for example, rotating and reciprocating piston metering pumps, peristaltic pumps or any other positive displacement pumps capable of dispensing micro-volumes of liquid with high accuracy. Alternatively, the dispenser may comprise a medical syringe, operated manually by a user of the apparatus.

In other preferred embodiments of the present invention, in particular those employing controlled-release capsules, the dispenser comprises a discrete feeder. Preferably, the feeder includes a capsule reservoir, a valve for controlling the passage of capsules, a detector which detects the passage of the capsules along the tube, and a controlled physiological fluid supply to convey the capsules along the tube from the reservoir to the distal end of the catheter.

In alternative preferred embodiments, the growth factor administration is performed by implanting or otherwise securing the catheter or a portion thereof within the myocardium for an extended period. The dispenser, for example, an osmotic pump, is preferably implanted within a patient's chest and is coupled to the portion of the catheter remaining in the heart, so as to provide treatment over the extended period. Optionally, the dispenser is placed external to the patient's body, and the proximal end of the catheter is connected extracorporeally to the dispenser.

There is therefore provided, in accordance with a preferred embodiment of the present invention, apparatus for intracardiac drug administration, including a catheter which is inserted into a chamber of the heart and brought into engagement with a site in the heart wall, the catheter including:

at least one position sensor, which generates signals responsive to the position of the catheter within the heart; and a drug delivery device, which administers a desired dose of a therapeutic drug at the site determined responsive to the signals from the position sensor.

Preferably, the therapeutic drug includes a growth factor. The drug is most preferably contained in a slow-release matrix, which preferably includes a solid capsule.

In a preferred embodiment, the catheter includes a contact sensor disposed on a distal surface of the catheter, which senses contact of the surface with the heart wall. Preferably, the contact sensor includes a pressure sensor.

Preferably, the position sensor includes a magnetic position sensor, which generates signals responsive to an externally-applied magnetic field.

Preferably, the position sensor signals are used to generate position and orientation coordinates, responsive to which the drug dose is delivered.

In a preferred embodiment, the catheter includes at least one physiological sensor, which generates signals indicative of the viability of heart tissue at the site. Preferably, the at least one physiological sensor includes an electrode. Further preferably, the apparatus generates a viability map of the heart based on the signals and administers the drug responsive thereto.

In another preferred embodiment, the apparatus includes a radiation source for irradiation of the myocardial tissue, wherein the catheter includes a waveguide, which communicates with the radiation source. Preferably, the drug delivery device administers the drug into a channel produced in the tissue by the irradiation, most preferably in the form of a solid capsule.

Preferably, the drug delivery device includes a hollow needle, which extends distally from the catheter and penetrates the heart tissue to deliver the drug dose.

In a preferred embodiment, the needle has a helical shape and is fastened to the site in the heart wall by a rotational movement of the needle.

Preferably, the needle is retracted into the catheter before and after the drug dose is delivered. Further preferably, the needle extends from the catheter through an opening in the catheter, which opening is covered by a puncture seal. Preferably, the drug delivery device includes a displacement mechanism, which extends and retracts the needle, wherein the displacement mechanism preferably controls the distance by which the needle extends from the catheter, so as to administer the drug at a predetermined depth within the heart wall.

In a preferred embodiment, the drug administration is controlled responsive to variations in the thickness of the heart wall at the site. Preferably, the catheter includes an ultrasound transducer, which generates signals indicative of the thickness of the heart wall, and the drug delivery device is gated to administer the drug when the wall at a predetermined thickness.

There is further provided, in accordance with another preferred embodiment of the present invention apparatus for intracardiac therapy, including:

a catheter, which is inserted into a chamber of the heart for administration of therapeutic treatment to the heart wall;

a sensor, which generates signals responsive to the thickness of the heart wall; and a controller, which receives the signals from the sensor and controls the treatment responsive the thickness of the heart wall.

Preferably, the sensor includes an ultrasound transducer, which is preferably fixed to the catheter adjacent to a distal end thereof.

Alternatively or additionally, the sensor includes a position sensor, which is fixed to the catheter adjacent to a distal end thereof.

In a preferred embodiment, the catheter includes a drug delivery device, and the treatment includes administration of a therapeutic substance at a site in the heart wall.

In another preferred embodiment, the apparatus includes a radiation source, wherein the treatment includes irradiation of the myocardial tissue using the source, and wherein the catheter includes a waveguide, which communicates with the radiation source.

Preferably, the controller gates the treatment so that the treatment is administered during a portion of the heart cycle. Preferably, the controller gates the treatment so that the treatment is administered when the thickness is at a maximum or alternatively, when the thickness is at a minimum.

There is moreover provided, in accordance with a preferred embodiment of the present invention, a method for intracardiac drug administration, including:

introducing a catheter into a chamber of the heart;
sensing position coordinates of the catheter;
positioning the catheter, using the coordinates, in engagement with the heart wall at a desired site; and
administering a therapeutic drug at the site using the catheter.

Preferably, administering the therapeutic drug includes administering a growth factor. Preferably, the growth factor includes a fibroblast growth factor (FGF) or alternatively, a vascular endothelial growth factor (VEGF). In a preferred embodiment, the growth factor includes a gene encoding the growth factor.

Preferably, administering the therapeutic drug includes injecting a slow-release preparation of the drug into the myocardium. Preferably, the slow-release preparation includes a liquid. Alternatively, the slow-release preparation includes a capsule containing the drug which is inserted into the myocardium.

In a preferred embodiment, the method includes irradiating the heart wall, preferably with laser radiation, for engendering revascularization of the myocardium. Preferably, irradiating the heart wall includes generating a channel in the myocardium, and administering the therapeutic drug includes inserting the drug into the channel.

In another preferred embodiment, positioning the catheter includes verifying contact between the catheter and the heart wall by receiving signals generated by a contact sensor disposed on the catheter.

Preferably, the method includes receiving physiological signals from the heart, wherein administering the therapeutic drug includes administering the drug responsive to the physiological signals. Preferably, the physiological signals include mechano-physiological signals or, alternatively or additionally, electrophysiological signals.

Preferably, administering the therapeutic drug includes administering the drug responsive to a measure of tissue viability determined from the physiological signals, so that administering the therapeutic drug preferably includes administering the drug substantially only in ischemic but viable areas of the heart. Further preferably, administering the therapeutic drug includes administering the drug responsive to a map of tissue viability.

Preferably, sensing the position coordinates includes sensing orientation coordinates of the catheter, and positioning the catheter includes orienting the catheter in a desired orientation relative to the heart wall responsive to the coordinates.

Further preferably, positioning the catheter includes positioning the catheter relative to a grid of points delineating a zone for drug administration on a geometrical map of the heart. Preferably sites are marked on the map at which the drug has been administered.

There is additionally provided, in accordance with a preferred embodiment of the present invention, a method of intracardiac therapy, including:

receiving signals indicative of variations in the thickness of a wall of the heart; and
administering a therapeutic treatment to a site in the heart wall responsive to the thickness variations.

Preferably, administering the treatment includes inserting a catheter into the heart and bringing the catheter into proximity with the site.

Further preferably, administering the treatment includes irradiating the heart wall with laser radiation conveyed via the catheter.

Additionally or alternatively, administering the treatment includes introducing a therapeutic drug into the heart wall using the catheter.

Preferably, receiving the signals includes receiving signals from a sensor fixed to the catheter, most preferably from a position sensor fixed to the catheter.

In a preferred embodiment, receiving the signals includes receiving ultrasound signals.

In another preferred embodiment, receiving the signals includes receiving electrophysiological signals.

Preferably, administering the treatment includes gating the treatment responsive to the thickness variations. Preferably, gating the treatment includes administering the treatment when the thickness is substantially at a maximum thereof during a cardiac cycle or alternatively, when the thickness is substantially at a maximum thereof during a cardiac cycle.

Additionally or alternatively, gating the treatment includes controing the treatment so that the treatment is applied at a desired depth within the heart wall.

The present invention will be more fully understood from the following detailed description of the preferred embodiments thereof, taken together with the drawings in which:

BRIEF DESCRIPTION OF THE DRAWINGS

FIG. 6B is a schematic, pictorial illustration showing a system for LMR and intracardiac drug delivery, including the catheter of FIG. 6A, in accordance with a preferred embodiment of the present invention; and FIG. 7 is a timing diagram showing signals associated with LMR treatment using the system of FIG. 6B, In accordance with a preferred embodiment of the present invention.

DETAILED DESCRIPTION OF PREFERRED EMBODIMENTS

Figure 1A:
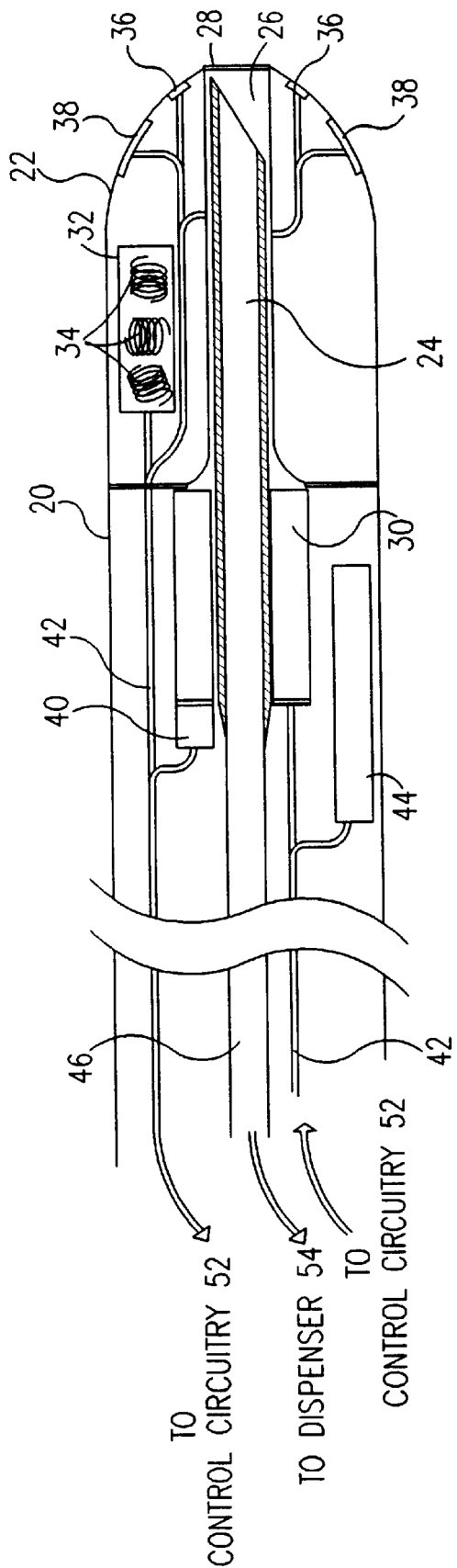
FIG. 1A is a schematic, partly sectional illustration of a catheter including a needle for intracardiac drug delivery, in a first, retracted configuration, in accordance with a preferred embodiment of the present invention.
Figure 1B:
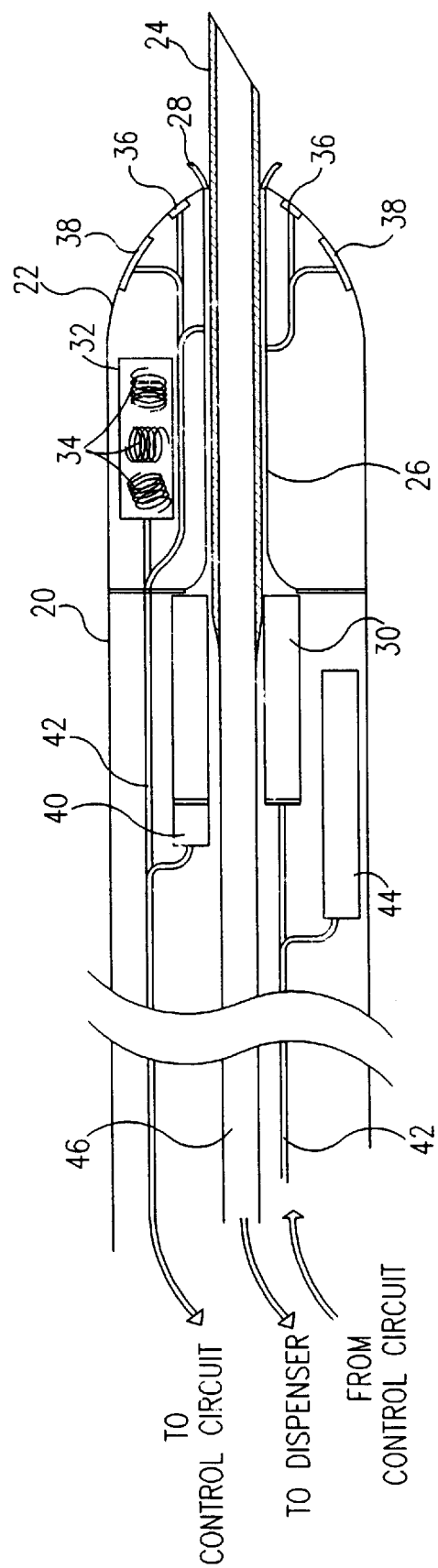
FIG. 1B is a schematic, partly sectional illustration showing the catheter of FIG. 1A in which the needle is in a second, extended configuration.

Reference is now made to FIGS. 1A and 1B, which are schematic, partly sectional illustrations of a catheter 20 for minimally invasive intracardiac drug delivery, in accordance with a preferred embodiment of the present invention. Catheter 20 comprises a hollow needle 24 within the catheter's distal end 22, for injection of a drug into the myocardium. In FIG. 1A, the needle is shown in a first configuration, in which it is retracted into a sheath 26 inside catheter 20, whereas in FIG. 1B, the needle extends distally out of distal end 22, for injection of the drug.

Preferably the drug comprises a growth factor, for example VEGF or bFGF, as described hereinabove. In a preferred embodiment, the drug comprises FGF-4 or FGF-5. In another preferred embodiment, the drug comprises a gene therapy agent, such as phVEGF. Needle 24 is connected via a duct 46 to a dispenser 54 (FIG. 2) which contains and the drug and dispenses it in predetermined doses through the needle.

Needle 24 preferably has an outer diameter of the order of 1 mm or less. In the extended configuration of FIG. 1B, the needle preferably extends 2–3 mm beyond the tip of distal end 22 of catheter 20. Sheath 26 is slightly wider than the outer diameter of the needle and is closed off at its distal end by a suitable seal 28, for example a silicon septum, which precludes back-flow of blood into the sheath and the catheter, while still allowing the needle to be repeatedly extended and retracted distally from the catheter. As long as needle 24 is retracted, it is fully contained within sheath 26, as shown in FIG. 1A, so that any contact between the needle and body tissue is substantially precluded. The needle is maintained in this retracted position during insertion of catheter 20 into the heart and removal therefrom, as well as while the catheter is being navigated from point to point within the heart, as described below.

A displacement mechanism 30 drives needle 24 distally out of distal end 22 to administer the drug, in the configuration shown in FIG. 1B, and withdraws the needle back to the position shown in FIG. 1A between administrations. Mechanism 30 preferably comprises a hydraulic piston with a suitably constrained stroke length, or an electromechanical device, such as a solenoid, or any other suitable remotely-driven mechanism known in the art, for example as described in the above-mentioned U.S. Pat. No. 4,578,061 and incorporated herein by reference. Alternatively, mechanism 30 may comprise a spring-loaded mechanism, which drives needle 24 into the endocardium when triggered and then pulls the needle back into sheath 26 after drug administration.

A needle sensor 40 is preferably coupled to mechanism 30 and/or needle 24 or duct 46. Sensor 40 preferably comprises a pressure transducer or other flow-metering device, as is known in the art, so as to sense any occlusion of the needle or flow obstruction in the duct, and to ensure that the proper dosage is delivered through the needle. Additionally or alternatively, sensor 40 comprises a microswitch or other mechanical sensor, for verifying that needle 24 is fully extended before injection of the drug and/or fully retracted before the catheter is moved.

Preferably, catheter 20 comprises a tip deflection mechanism 44, for steering and navigating distal end 22. Preferably, mechanism 44 is operated by one or more pull-wires (not shown in the figures), as described in the above-mentioned U.S. Provisional Patent Application No. 60/042,872. Alternatively, mechanism 44 may be of any suitable type known in the art, such as are described in the above-mentioned PCT Patent Application PCT/US95/01103 or U.S. Pat. Nos. 5,404,297, 5,368,592, 5,431,168, 5,383, 923, 5,368,564, 4,921,482 and 5,195,968.

Catheter 20 further comprises a position sensor 32, for determination of position and orientation coordinates of distal end 22. Preferably, sensor 32 comprises a magnetic position sensor including coils 34, which generate signals responsive to an externally-applied magnetic field, as described in the above-mentioned PCT publication WO96/05768. The catheter is navigated and located using the position sensor, so as to deliver the drug, preferably the chosen growth factor, at designated, accurately-chosen sites in the endocardium. Catheter 20 thus allows precise, local delivery of the drug, which is required for effective administration of growth factors, in a minimally invasive manner that cannot be accomplished using apparatus and methods known in the art.

Preferably, catheter 20 also comprises one or more contact sensors 36, for example, pressure sensors, which generate signals responsive to contact between distal end 22 and the heart wall so to assure proper contact between the catheter and the wall before extension of needle 24. Additionally, the catheter may comprise one or more electrodes 38, which are used to measure electrical activity in the heart wall, in order to assess and map the local viability of the heart tissue. Methods of viability mapping are described in greater detail, for example, in PCT Patent Application PCT/IL97/00010, and in U.S. Pat. No. 5,568,809, mentioned above. A viability map may be generated either prior to or concurrently with the drug administration, as described hereinbelow.

Figure 1C:
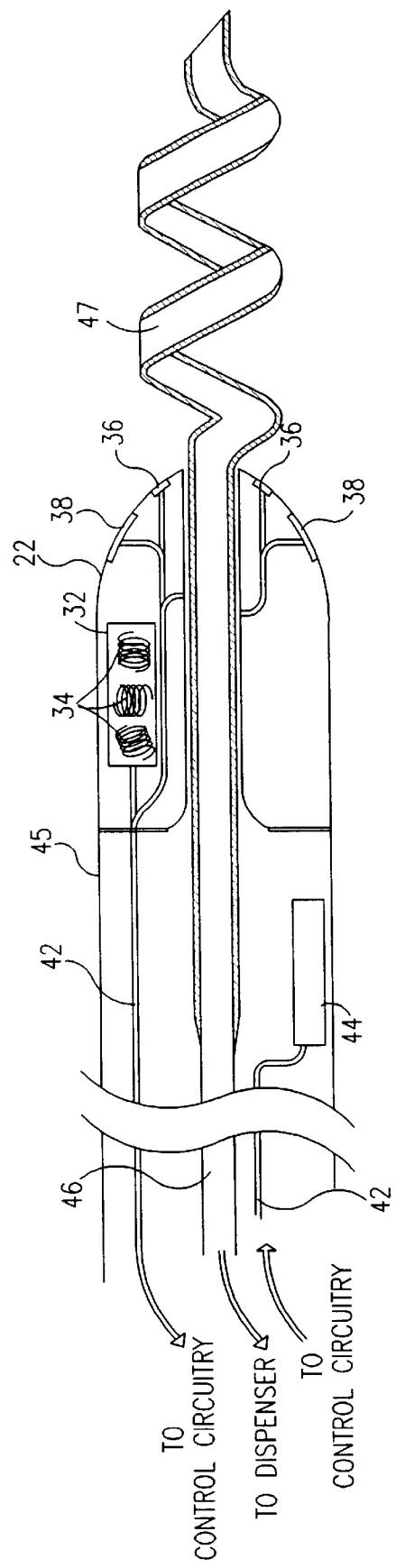
FIG. 1C is a schematic, partly sectional illustration of a catheter including a needle for intracardiac drug delivery, in accordance with an alternative preferred embodiment of the present invention.

FIG. 1C is a schematic, partly sectional illustration of a catheter 45 for intracardiac drug delivery, in accordance with an alternative preferred embodiment of the present invention. Catheter 45 is substantially similar to catheter 20, described above, except that catheter 45 includes a spiral needle 47. After the catheter is brought into engagement with a site in the heart wall where the drug is to be delivered, needle 47 is screwed into the wall by a corkscrew-like rotational movement. The movement may be achieved either by rotation of the needle within the catheter or rotation of the entire catheter. Screwing the needle into the heart wall ensures that catheter 45 will remain firmly in place during the drug administration.

In another preferred embodiment, not shown in the figures, catheter 45 has a helical or cylindrical cavity in distal end 22, which enables needle 47 to be retracted into the catheter during insertion of the catheter into the heart and, preferably, during movement of the catheter from one drug administration site to another inside the heart.

Figure 2:
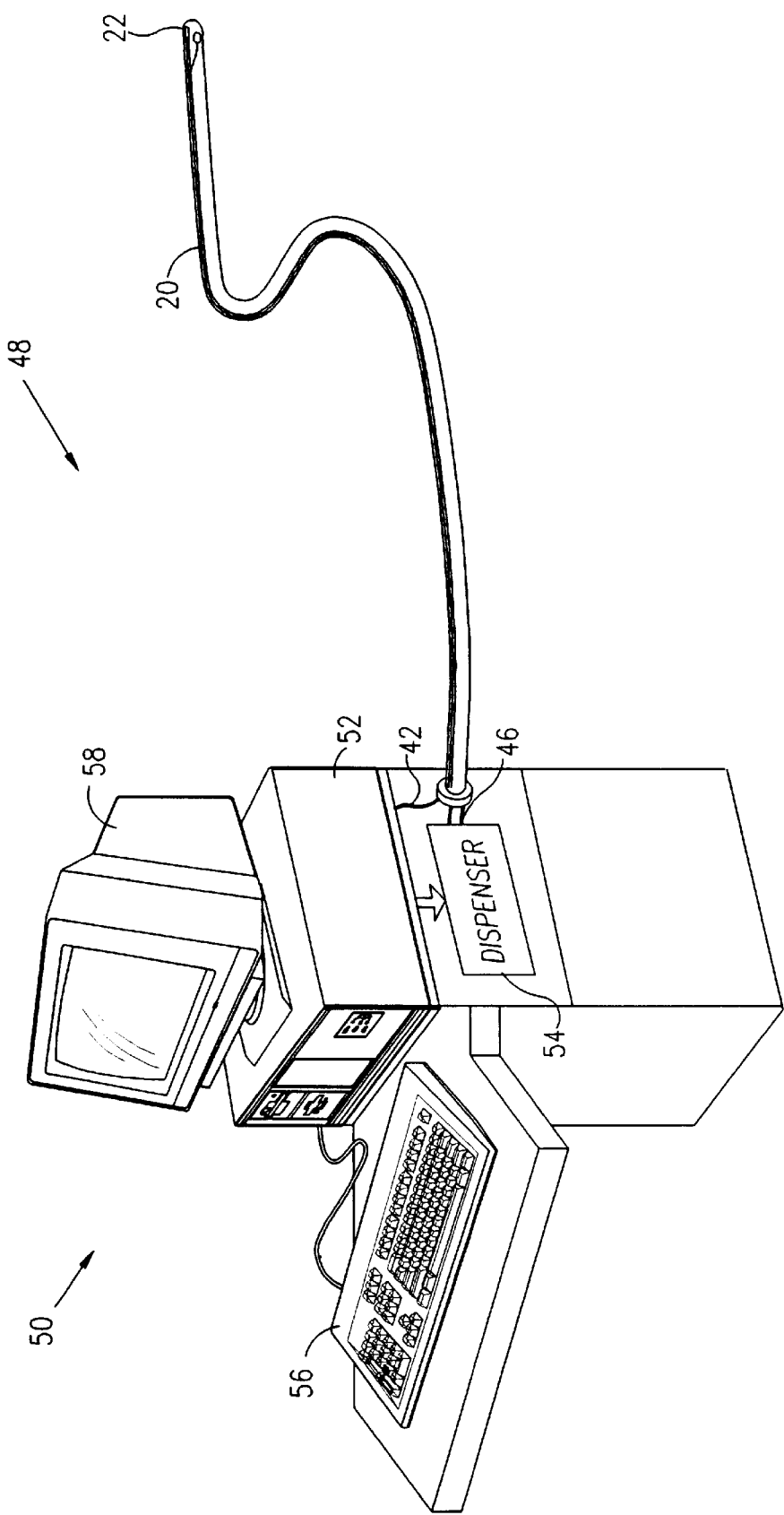
FIG. 2 is a schematic, pictorial illustration showing a system for intracardiac drug delivery, including the catheter of FIGS. 1A and 1B, in accordance with a preferred embodiment of the present invention.

FIG. 2 is a schematic, pictorial illustration showing a system 48 for intracardiac drug delivery, in accordance with a preferred embodiment of the present invention. System 48 comprises a console 50 to which catheter 20 is connected at a proximal end thereof. The console includes control circuitry 52, preferably comprising a computer, to which a user input device 56 and a display 58 are preferably coupled, so as to allow a user, generally a physician, to interact with and operate the system. The circuitry is coupled via wires 42 to elements of catheter 20, including sensors 32, 36, 38 and 40, as well as mechanisms 30 and 44, as shown in FIGS. 1A and 1B.

Figure 6A:
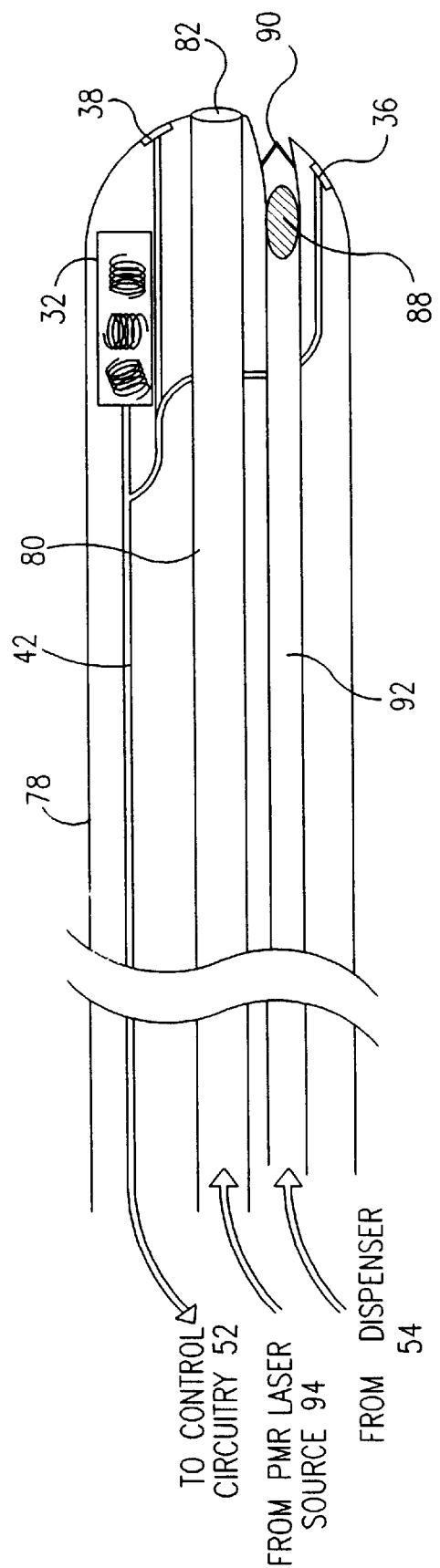
FIG. 6A is a schematic, partly sectional illustration of a catheter for use in performing concurrent laser myocardial revascularization (LMR) and intracardiac drug delivery, in accordance with a preferred embodiment of the present invention.

Console 50 also comprises a dispenser 54, which is coupled via duct 46 to dispense the drug in predetermined doses through needle 24. Preferably, dispenser 54 comprises a reservoir into which the drug is filled, in liquid form, and a fluid metering pump communicating with the reservoir. The pump may comprise a rotating or reciprocating piston metering pump, a peristaltic pump or any other suitable positive displacement pump known in the art, for example, a PiP valveless piston pump, manufactured by Fluid Metering Inc. of Oyster Bay, N.Y. Alternatively, dispenser 54 may comprise a discrete feeder, for controlling the passage of microcapsules from the reservoir through the catheter, as is likewise known in the art. The microcapsules are implanted in the myocardium, for example, as shown in FIG. 6A below and described further with reference thereto.

Preferably, circuitry 52 generates a map of the heart, preferably a viability map, which is displayed on display 58. Such a viability map is useful in identifying suitable candidate areas for drug administration, i.e., ischemic but still viable areas of the heart tissue, to which growth factor therapy could most usefully be applied, as opposed to infarcted and non-viable areas or to well-perfused and healthy areas, for which growth factor therapy would either be unuseful or toxic. Circuitry 52 determines and marks a grid of points on the map, covering a candidate area at a desired density (point-to-point spacing), at which the drug is to be administered. The viability map may be generated in a separate procedure, before insertion of catheter 20 for administration of the drug, but is preferably generated concurrently with or immediately prior to drug administration, making use of position sensor 32 and electrode 38 to map the heart's electrical activity.

Figure 3:
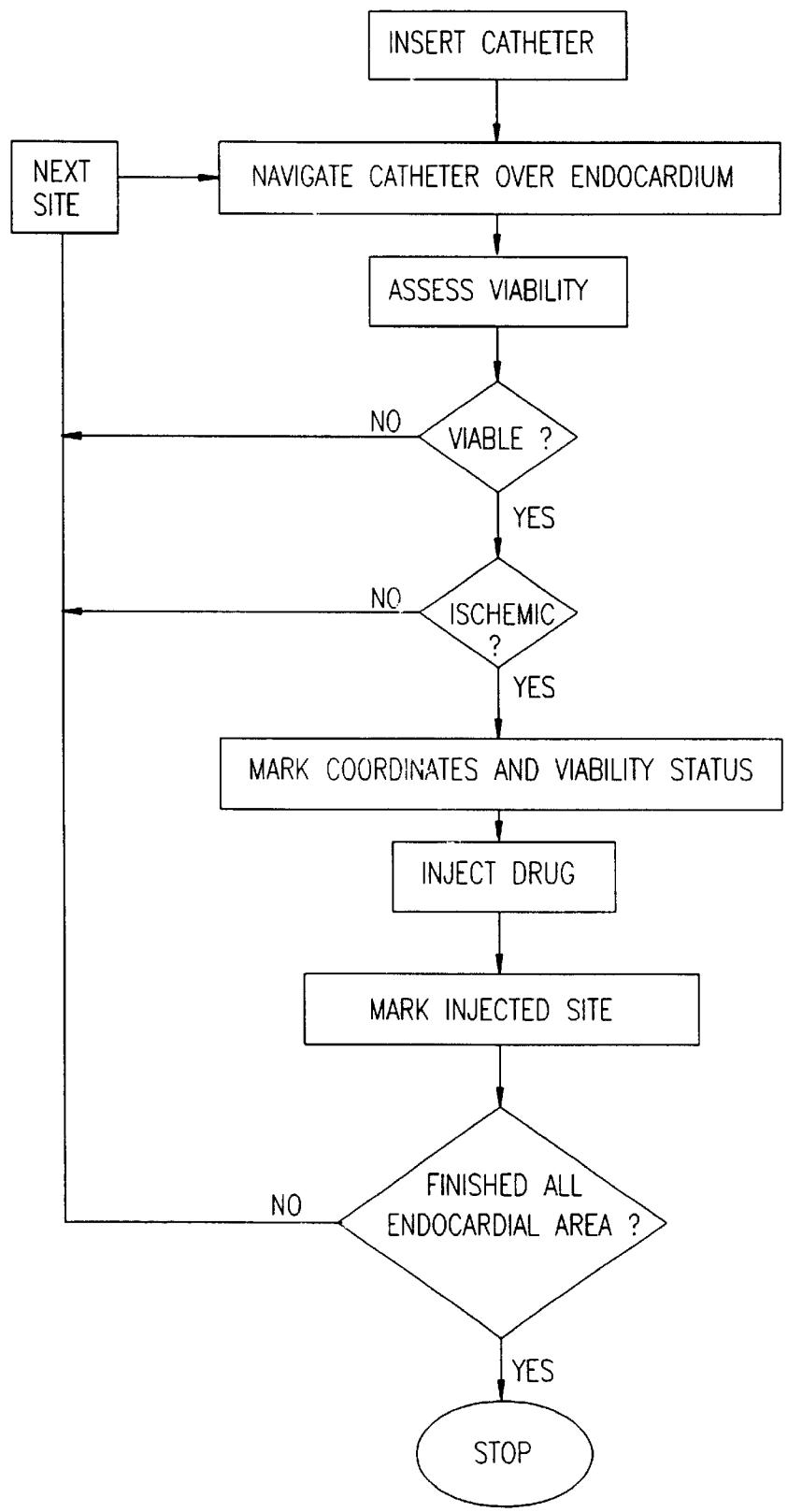
FIG. 3 is a flowchart illustrating a method of operation of the system of FIG. 2, in accordance with a preferred embodiment of the present invention.

FIG. 3 is a flow chart showing a method for concurrent viability mapping and drug administration, using system 48 and catheter 20, in accordance with a preferred embodiment of the present invention. The catheter is inserted into the heart, preferably percutaneously, and is navigated, either automatically or under user control, to a candidate area for drug administration. Using position sensor 32, distal end 22 is positioned against the endocardium, generally perpendicular to the surface thereof, at a candidate location for drug administration. Preferably, circuitry 52 receives and analyzes signals from contact sensors 36 to ensure positive contact between the catheter's distal end and the endocardium. Alternatively or additionally, circuitry 52 may receive readings from the position sensor over several cardiac cycles, and to the extent that the position coordinates thus determined remain substantially constant (for any given phase of the cardiac cycle), it is assumed that distal end 22 is in positive contact with the endocardium.

Once distal end 22 is securely positioned, circuitry 52 assesses the viability of the heart tissue at the location of the distal end, preferably based on the waveform and amplitude of electrogram signals received by electrodes 38. A motion profile of the heart wall at the location may also be generated, by taking position readings from sensor 32 at multiple phases of the heart cycle and may be used, as well, is the viability assessment. In this manner, circuitry 52 preferably verifies that the heart tissue in a vicinity of the location of distal end 22 is ischemic but still viable before administering the drug at the location. As noted hereinabove, administration of drugs, such as growth factors, to non-ischemic areas of the heart can have deleterious effects, and generally speaking, it is desirable to apply no more than the precise dosage required in order to avoid possible systemic toxicity. For these reasons, circuitry 52 preferably prevents administration of the drug at locations that do not meet the criteria of viability described above, or at least notifies the user of the viability status of such locations.

Once it has been ascertained that distal end 22 of catheter 20 is firmly positioned at an ischemic site, needle 24 is extended out of sheath 26, as shown in FIG. 1B, and a dose of the drug is administered. Circuitry 52 marks the location, viability status and dosage information on the map of the heart, and the catheter is moved on to the next point on the grid. The procedure preferably continues until the entire candidate area has been covered, whereupon the catheter is withdrawn from the heart. The viability mapping procedure may be repeated at a later date in order to assess the effectiveness of the drug treatment and, if necessary, administer additional dosage thereof.

Catheter 20 may, additionally or alternatively, include other types of sensors, for use in controlling and/or monitoring the drug administration and in viability mapping of the heart. Mapping catheters having sensors of various types described, for example, in the above-mentioned PCT Patent Application PCT/IL97/00010 and U.S. Pat. No. 5,568,809. Other physiological detectors may be employed, as well, for example, perfusion detectors, which measure local microcirculation blood flow rates, or optical detectors, which sense fluorescent emission related to local blood perfusion.

Figure 4:
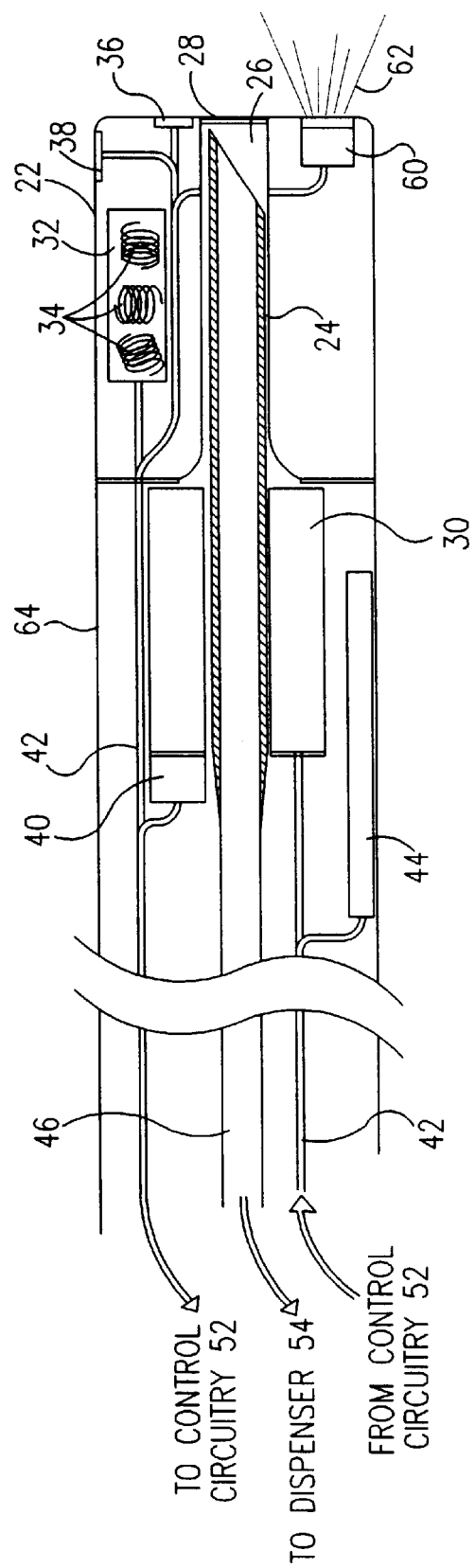
FIG. 4 is a schematic, partly sectional illustration of a catheter for use in intracardiac drug delivery, in accordance with an alternative preferred embodiment of the present invention.

FIG. 4 is a schematic, partly sectional illustration of another catheter 64 for intracardiac drug injection, in accordance with a preferred embodiment of the present invention. Catheter 64 is generally similar to catheter 20, described above, but also includes an ultrasound transducer 60, which emits a beam of ultrasonic radiation 62 and receives ultrasound waves reflected from the heart wall. Transducer 60 is preferably used to measure and map the thickness of the heart wall, as described in the above-mentioned PCT patent application PCT/US95/01103. Alternatively or additionally, the transducer may be used to produce an ultrasound image of the endocardial and/or endocardial surface. In this case, the transducer preferably comprises an array of transducer elements, so that a detailed image can be produced with high resolution.

Figure 5:
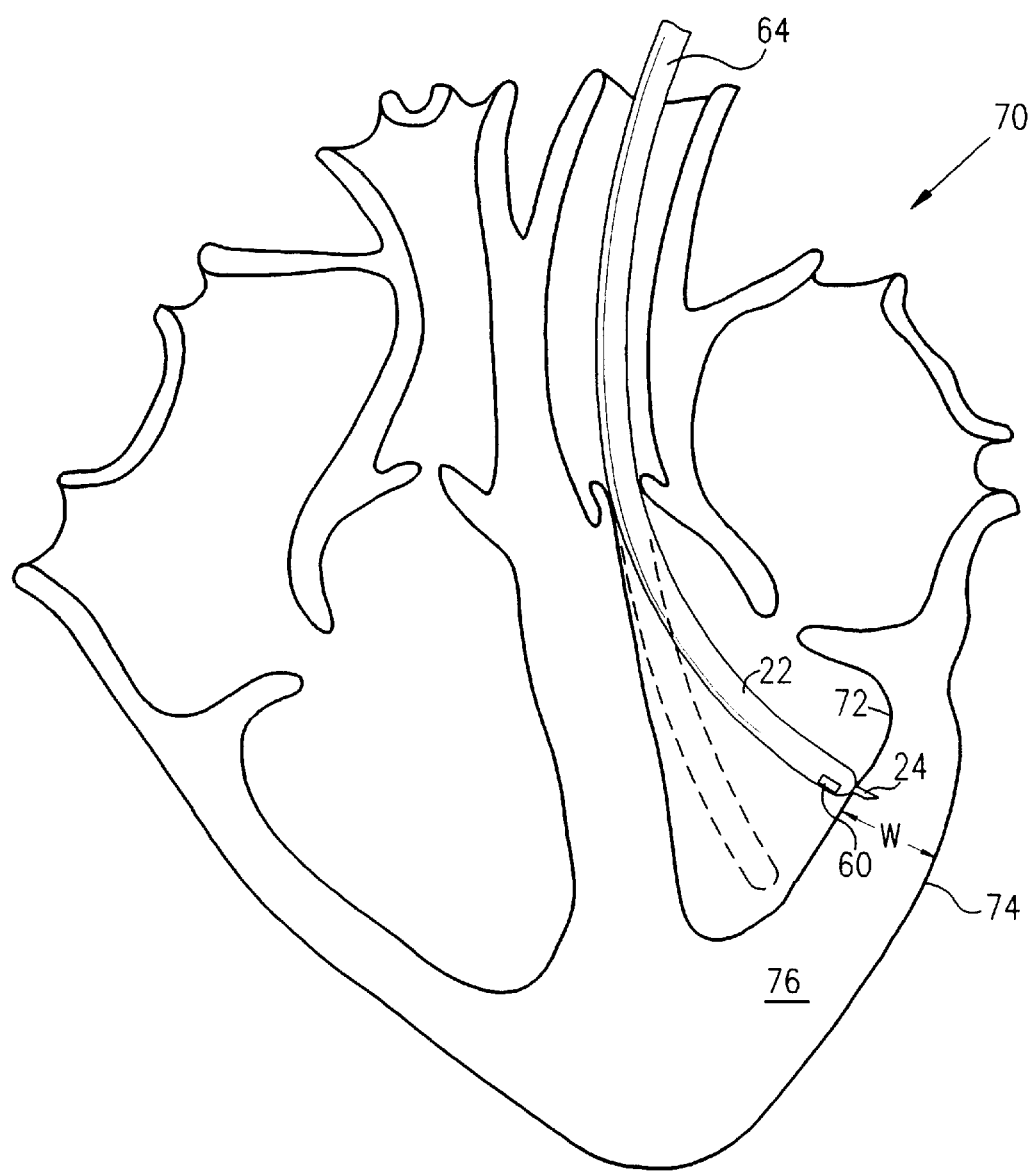
FIG. 5 is a schematic, sectional illustration of a human heart, in which the catheter of FIG. 4 is inserted for delivery of a drug thereto, in accordance with a preferred embodiment of the present invention.

FIG. 5 is a schematic, sectional illustration of a heart 70 into which catheter 64 is inserted, for administering a drug thereto. As described above, distal end 22 of catheter 64 is brought into engagement with endocardium 72. Ultrasound signals received by transducer 60 are used to measure the distance from the endocardium to the outer surface of epicardium 74, so that the thickness W of the heart wall is determined. Assuming that distal end 22 is properly positioned at a suitable, viable location for drug administration, needle 24 is extended out of the catheter into myocardium 76.

Preferably, dispensing of the drug through needle 24 is gated responsive to changes in the thickness of the wall. It is believed that optimal dispersion and retention of the drug within myocardium 76 is generally achieved when the needle dispenses the drug roughly midway through the myocardium. The thickness of the heart wall varies, however, as the heart contracts and expands, and this variation may be measured using transducer 60. Since the length of the needle is known, the drug is preferably dispensed when the thickness W of the wall is approximately equal to at least twice the length of the needle extending out of the catheter, as shown in FIG. 5. Alternatively, dispensing of the drug may be gated at any desired wall thickness, and the drug may be dispensed at substantially any desired depth within the heart wall. Further alternatively or additionally, the depth of insertion of needle 24 may be controlled responsive to the thickness W, so that the greater the thickness, the deeper is the needle inserted.

FIG. 6A schematically illustrates distal end 22 of a catheter 78 for combined performance of laser myocardial revascularization (LMR) and intracardiac drug administration, in accordance with another preferred embodiment of the present invention. FIG. 6B is a schematic, pictorial illustration of a system 96 for combined LMR and drug therapy, using catheter 78. System 96 comprises control console 50, substantially as described above with reference to FIG. 2, except that in system 96 the console also includes a laser source 94 for use in the LMR procedure.

In the embodiment of FIGS. 6A and 6B, the drug to be administered, preferably comprising a growth factor, is preferably incorporated within a solid polymeric matrix capsule 88. The capsule is passed from dispenser 54 within a suitably pressurized carrier fluid through a channel 92 running along the catheter and is inserted using the catheter into the heart wall. A one-way valve 90 preferably closes off the distal end of channel 92, allowing capsule 88 to exit therefrom, but preventing blood or debris from entering and possibly clogging the channel.

Catheter 78 also comprises a waveguide 80 connected proximally to laser source 94 and distally to optics 82, which focus radiation from the laser source into the heart wall. Catheter 78 preferably comprises position sensor 32 and one or more contact sensors 36 and/or electrodes 38, as well as a steering mechanism (not shown in FIG. 6A), as described above. Catheter 78 is preferably fed percutaneously through a blood vessel, such as the aorta, into a chamber of the heart and navigated to an ischemic area of the heart using the steering mechanism and the position sensor.

At each point on a grid in the ischemic area, as determined and designated on a map of the heart by control circuitry 52, laser source 94 is activated to generate a revascularizing channel within the myocardium, as described, for example, in the above-mentioned PCT/IL97/00011 patent application. Upon generation of the channel, a slow-release capsule 88, designed to fit within the LMR channel, is ejected from duct 92, which is provided with a suitably curved distal portion, through valve 90. Alternatively, the drug may be dispensed using any other suitable type of solid capsule delivery system known in the art, for example, as described in U.S. Pat. Nos. 4,588,395 and 4,578,061, mentioned above.

Preferably, capsule 88 is designed so that its dimensions remain substantially constant throughout the treatment period, so as to secure the capsule in place at the designated location and preclude accidental drift, thus assuring appropriate localized administration of the drug throughout the treatment duration. Further preferably, the medium in which the growth factor is embedded comprises a biocompatible polymeric matrix along with other auxiliary agents, for example heparin, as described in the above-mentioned articles by Harada et al and by Isner. The growth factor is leached out of the capsule by myocardial blood circulation, due to an osmotic gradient between the capsule and the surrounding tissue, and is dispersed within the tissue. Preferably, the capsule is designed to disintegrate upon completion of the treatment, by employing a suitable mechanism. For example, the matrix solubility may be coordinated with the drug diffusion rate, or a fast matrix solubility may be triggered in response to a certain concentration level of a predetermined component. Thus, upon reaching the treatment's end-point, the capsule is rapidly dissolved and its components washed away.

Although catheter 78 is described hereinabove as delivering solid drug capsules concomitantly with LMR irradiation, it will be understood that each of these elements can be used independently of the other is drug administration protocols. For example, capsule 88 may be implanted in the heart wall using a needle (like needle 24, suitably adapted) or other microsurgical implement, or by means of a burst of pressure through duct 92.

Further alternatively, the LMR therapy may be performed in conjunction with administration of a drug, such as a growth factor, in a liquid matrix. In this case, a needle, such as needle 24, punctures the heart wall and administers the drug at a site in the vicinity of the LMR channel, such that the channel's borders are within a radius of influence of the growth factor during at least a major portion of the drug's therapeutic life. The use of the growth factor and LMR together is believed to further facilitate angiogenesis, as mentioned above.

FIG. 7 is a timing diagram, which schematically illustrates signals used in controlling laser source 94, in accordance with a preferred embodiment of the present invention. The laser source is triggered responsive to an ECG signal, received either from body surface electrodes on the skin of a patient undergoing the therapy, or from electrode 38 on catheter 78. Triggering the laser in this manner ensures that the laser pulse will be fired into the myocardium when the heart wall is at a certain, desired thickness, preferably at its greatest thickness, during systole.

As shown in FIG. 7, after catheter 78 is suitably positioned against the endocardium, the ECG R-wave peak is detected, and a position reading is taken from position sensor 32 within a short time, preferably 20–50 msec thereafter. The R-wave is detected and position readings are taken for several heart cycles in succession. Circuitry 52 tests the R—R intervals of successive cycles, and also compares the successive position readings. The purpose of this comparison is to ensure that the both the patient's heart rhythm and the positioning of distal end 22 are stable before firing the laser. Therefore, circuitry 52 enables laser source 94 only if the R—R interval is within a predetermined limit of the interval in two or more preceding cycles, preferably within ±12% or 120 msec, and if the position reading from sensor 32 has not shifted by more than a predetermined distance, preferably in the range of 0–12 mm, most preferably in the range of 3–6 mm.

After circuitry 52 has verified the stable heart rhythm and catheter position, it provides a laser enable pulse once every heart cycle, at a predetermined delay following the detection of the R-wave in each cycle. The delay is adjusted, either automatically by circuitry 52 or by the user of system 96, so that the laser will fire only at a point in the heart cycle at which the heart wall has a desired thickness. When the user activates a laser switch on console 50, the laser fires a train of one or more radiation pulses in response to each laser enable pulse provided by circuitry 52. Due to delays inherent in high-voltage electronics used to drive laser source 94, the laser pulse train will generally be delayed relative to the rising edge of the laser enable pulse by an insignificant, random delay, generally about 5–25 msec.

Optionally, an ultrasound transducer, such as transducer 60 shown in FIG. 4, is used to measure the thickness, so as to trigger laser source 94 accordingly. Alternatively or additionally, variations in the position readings received from sensor 32 in the course of a heart cycle may be used to estimate the heart wall thickness and/or trigger the laser. In any case, the laser is preferably controlled to fire when the heart wall is at its thickest, so as to create a relatively wide channel in the myocardium while reducing the risk that the channel will penetrate through the epicardium.

It will be appreciated that the preferred embodiments described above are cited by way of example, and the full scope of the invention is limited only by the claims.

What is claimed is:

1. Apparatus for intracardiac drug administration, comprising a catheter which is inserted into a chamber of the heart and brought into engagement with a site in the heart wall, the catheter comprising:

at least one position sensor at a distal end of the catheter for determining position and orientation coordinates of the distal end of the catheter by generating signals responsive to the position of the distal end of the catheter within the heart; and a drug delivery device, which administers a desired dose of a therapeutic drug at the site determined responsive to the signals from the position sensor.

2. Apparatus according to claim 1, further in combination with a therapeutic drug, wherein the therapeutic drug comprises a growth factor.

3. Apparatus according to claim 1, further in combination with a therapeutic drug, wherein the drug is contained in a slow-release matrix.

4. Apparatus according to claim 3, wherein the matrix comprises a solid capsule.

5. Apparatus according to claim 1, wherein the catheter comprises a contact sensor disposed on a distal surface of the catheter, which senses contact of the surface with the heart wall.

6. Apparatus according to claim 5, wherein the contact sensor comprises a pressure sensor.

7. Apparatus according to claim 1, wherein the position sensor comprises a magnetic position sensor, which generates signals responsive to an externally- applied magnetic field.

8. Apparatus according to claim 1, wherein the catheter comprises at least one physiological sensor, which generates signals indicative of the viability of heart tissue at the site.

9. Apparatus according to claim 8, wherein the at least one physiological sensor comprises an electrode.

10. Apparatus according to claim 8, further in combination with a therapeutic drug, wherein the apparatus generates a viability map of the heart based on the signals and administers the drug responsive thereto.

11. Apparatus according to claim 1, and comprising a radiation source for irradiation of the myocardial tissue, wherein the catheter comprises a waveguide, which communicates with the radiation source.

12. Apparatus according to claim 11, further in combination with a therapeutic drug, wherein the drug delivery device administers the drug into a channel produced in the tissue by the irradiation.

13. Apparatus according to claim 12, wherein the drug is a solid capsule.

14. Apparatus according to claim 1, further in combination with a therapeutic drug, wherein the drug delivery device comprises a hollow needle, which extends distally from the catheter and penetrates the heart tissue to deliver the drug dose.

15. Apparatus according to claim 14, wherein the needle has a helical shape.

16. Apparatus according to claim 15, wherein the needle is adapted to be fastened to the site in the heart wall by a rotational movement of the needle.

17. Apparatus according to claim 14, wherein the needle is retracted into the catheter before and after the drug dose is delivered.

18. Apparatus according to claim 17, wherein the needle extends from the catheter through an opening in the catheter, which opening is covered by a puncture seal.

19. Apparatus according to claim 18, wherein the drug delivery device comprises a displacement mechanism, which extends and retracts the needle.

20. Apparatus according to claim 19, wherein the displacement mechanism controls the distance by which the needle extends from the catheter, so as to administer the drug at a predetermined depth within the heart wall.

21. Apparatus according to claim 1, wherein the drug administration is controlled responsive to variations in the thickness of the heart wall at the site.

22. Apparatus according to claim 21, wherein the catheter comprises an ultrasound transducer, which generates signals indicative of the thickness of the heart wall.

23. Apparatus according to claim 21, wherein the drug delivery device is gated to administer the drug when the wall at a predetermined thickness.

24. Apparatus according to claim 1, further in combination with a therapeutic drug, wherein the therapeutic drug comprises a liquid compound.

25. Apparatus according to claim 1, further in combination with a therapeutic drug, wherein the therapeutic drug comprises a soluble compound.

26. Apparatus according to claim 1, further in combination with a therapeutic drug, wherein the therapeutic drug comprises a gene encoding a growth factor.

27. Apparatus according to claim 1, further in combination with a therapeutic drug, wherein the therapeutic drug comprises naked DNA.

28. Apparatus according to claim 27, further in combination with a therapeutic drug, wherein the therapeutic drug comprises plasmid DNA.

29. Apparatus according to claim 1, further in combination with a therapeutic drug, wherein the therapeutic drug comprises an adenoviral vector.

30. Apparatus according to claim 2, wherein the growth factor comprises a vascular endothelial growth factor (VEGF).

31. Apparatus according to claim 2, wherein the growth factor comprises a fibroblast growth factor (FGF).

32. Apparatus according to claim 4, wherein the matrix is a biocompatible polymeric matrix.

33. Apparatus according to claim 32, wherein the capsule also includes an auxiliary agent.

34. Apparatus according to claim 1, wherein said agent comprises heparin.

35. Apparatus according to claim 1, wherein said drug delivery device administers said therapeutic drug by a burst of pressure.

36. Apparatus according to claim 17, wherein said needle is retracted during insertion of said catheter into said heart.

37. Apparatus according to claim 5, wherein the position sensor is used to position a distal end of the catheter generally perpendicular to the site in the heart wall.

38. Apparatus according to claim 37, further comprising control circuitry for ensuring contact between the distal end of the catheter and the site in the heart wall.

39. Apparatus according to claim 1, wherein the at least one position sensor generates signals responsive to an externally-applied field.

40. Apparatus according to claim 39, wherein the at least one position sensor is a magnetic position sensor.

41. Apparatus for intracardiac drug administration, comprising a catheter which is inserted into a chamber of the heart and brought into engagement with a site in the heart wall, the catheter comprising:

at least one magnetic position sensor for determining position coordinates of the catheter by generating signals responsive to the position of the catheter within the heart; and a drug delivery device, which administers a desired dose of a therapeutic drug at the site determined responsive to the signals from the position sensor.

42. Apparatus according to claim 41, wherein the magnetic position sensor generates signals responsive to an externally-applied field.

43. Apparatus for intracardiac drug administration, comprising a catheter which is inserted into a chamber of the heart and brought into engagement with a site in the heart wall, the catheter comprising:

at least one position sensor for determining position coordinates of the catheter by generating signals relating to the position of the catheter within the heart responsive to an externally-applied field; and a drug delivery device, which administers a desired dose of a therapeutic drug at the site determined responsive to the signals from the position sensor.

44. Apparatus according to claim 43, wherein the at least one position sensor determines position and orientation coordinates.

45. Apparatus according to claim 44, wherein the at least one position sensor is a magnetic position sensor.

46. A method for intracardiac drug administration, comprising:

providing a catheter having at least one magnetic position sensor;

introducing the catheter into a chamber of the heart;

sensing position coordinates of the catheter with the magnetic position sensor;

positioning the catheter, using the coordinates, in engagement with the heart wall at a desired site; and administering a therapeutic drug at the site using the catheter.

47. A method according to claim 46, including applying an externally-applied field.

48. A method according to claim 47, including applying an externally-applied magnetic field.

49. A method for intracardiac drug administration, comprising:

providing a catheter having at least one position sensor;

applying an externally-applied field;

introducing the catheter into a chamber of the heart;

sensing position coordinates of the catheter with the at least one position sensor responsive to the externally-applied field;

positioning the catheter, using the coordinates, in engagement with the heart wall at a desired site; and administering a therapeutic drug at the site using the catheter.

50. A method according to claim 49, including sensing position and orientation coordinates of the catheter.

51. A method according to claim 50, including applying an externally-applied magnetic field.

52. A method for intracardiac drug administration, comprising:

providing a catheter having at least one position sensor at a distal end of the catheter;

introducing the catheter into a chamber of the heart;

sensing position and orientation coordinates of the distal end of the catheter with the at least one position sensor;

positioning the distal end of the catheter, using the position and orientation coordinates, in engagement with the heart wall at a desired site; and administering a therapeutic drug at the site using the catheter.

53. A method according to claim 52, further comprising administering a growth factor at the site using the catheter.

54. A method according to claim 53, further comprising administering a fibroblast growth factor (FGF) at the site using the catheter.

55. A method according to claim 53, further comprising administering a vascular endothelial growth factor (VEGF) at the site using the catheter.

56. A method according to claim 53, further comprising administering a gene encoding the growth factor at the site using the catheter.

57. A method according to claim 52, wherein administering the therapeutic drug comprises injecting a slow-release preparation of the drug into the myocardium.

58. A method according to claim 57, wherein administering the slow-release preparation comprises administering a liquid.

59. A method according to claim 57, wherein administering the slow-release preparation comprises inserting a capsule containing the drug into the myocardium.

60. A method according to claim 52, and comprising irradiating the heart wall for engendering revascularization of the myocardium.

61. A method according to claim 60, wherein irradiating the heart wall comprises generating a channel in the myocardium, and wherein administering the therapeutic drug comprises inserting the drug into the channel.

62. A method according to claim 52, wherein positioning the catheter comprises verifying contact between the catheter and the heart wall by receiving signals generated by a contact sensor disposed on the catheter.

63. A method according to claim 52, and comprising receiving physiological signals from the heart, wherein administering the therapeutic drug comprises administering the drug responsive to the physiological signals.

64. A method according to claim 63, further comprising receiving mechano-physiological signals from the heart.

65. A method according to claim 63, further comprising receiving electrophysiological signals from the heart.

66. A method according to claim 63, wherein administering the therapeutic drug comprises administering the drug responsive to a measure of tissue viability determined from the physiological signals.

67. A method according to claim 66, wherein administering the therapeutic drug comprises administering the drug substantially only in ischemic but viable areas of the heart.

68. A method according to claim 66, wherein administering the therapeutic drug comprises administering the drug responsive to a map of tissue viability.

69. A method according to claim 52, further comprising orienting the catheter in a desired orientation relative to the heart wall responsive to the position and orientation coordinates.

70. A method according to claim 52, wherein positioning the catheter comprises positioning the catheter relative to a grid of points delineating a zone for drug administration on a geometrical map of the heart.

71. A method according to claim 70, and comprising marking sites on the map at which the drug has been administered.

72. A method according to claim 52, wherein administering the therapeutic drug comprises administering a liquid compound.

73. A method according to claim 52, wherein administering the therapeutic drug comprises administering a soluble compound.

74. A method according to claim 52, wherein administering the therapeutic drug comprises administering naked DNA.

75. A method according to claim 74, wherein administering the therapeutic drug comprises administering plasmid DNA.

76. A method according to claim 52, wherein administering the therapeutic drug comprises administering an adenoviral vector.

77. A method according to claim 59, further comprising inserting a capsule including a biocompatible polymeric matrix containing the drug into the myocardium.

78. A method according to claim 77, further comprising including an auxiliary agent in the capsule.

79. A method according to claim 78, further comprising including heparin in the capsule.

80. A method according to claim 52, further comprising administering said therapeutic drug by a burst of pressure.

81. A method according to claim 52, further comprising administering said therapeutic drug multiple times in said heart.

82. Method according to claim 62, wherein the catheter is positioned generally perpendicular to the desired site in the heart wall.

83. Method according to claim 82, including verifying contact between the catheter and the desired site in the heart wall through control circuitry.

84. A method according to claim 52, including applying an externally-applied field.

85. A method according to claim 84, including applying an externally-applied magnetic field.

* * * * *

UNITED STATES PATENT AND TRADEMARK OFFICE
CERTIFICATE OF CORRECTION

PATENT NO.     : 6,309,370 B1                                              Page 1 of 1
DATED          : October 30, 2001
INVENTOR(S)    : Shlomo Ben-Haim, Uri Yaron and Avraham Matcovitch It is certified that error appears in the above-identified patent and that said Letters Patent is hereby corrected as shown below:

<u>Title page,</u>
Item [12], reads: "[12] United States Patent, Haim et al," should be
-- [12] United States Patent, Ben-Haim et al. --

Item [75], reads: [75] Inventor(s): Shlomo Ben Haim, Haifa, Uri Yaron, Zichron Yaakov; Avraham Matcovitch, Nesher, all of (IL)" should be
-- [75] Inventor(s): Shlomo Ben-Haim, Haifa; Uri Yaron, Zichron Yaakov: Avraham Matcovitch, Nesher, all of (IL) --

Signed and Sealed this

Sixth Day of August, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.   : 6,309,370 B1
DATED        : October 30, 2001
INVENTOR(S)  : Shlomo Ben-Haim, Uri Yaron and Avraham Matcovitch It is certified that error appears in the above-identified patent and that said Letters Patent is hereby corrected as shown below:

Column 18,
Line 18, please insert the word -- is -- after "wall"

Signed and Sealed this

Twenty-sixth Day of August, 2003

JAMES E. ROGAN
*Director of the United States Patent and Trademark Office*